(12) United States Patent
Mayse

(10) Patent No.: US 11,607,303 B2
(45) Date of Patent: *Mar. 21, 2023

(54) DEVICES, SYSTEMS, AND METHODS FOR TREATING PULMONARY DISEASE

(71) Applicant: Apreo Health, Inc., Menlo Park, CA (US)

(72) Inventor: Martin Mayse, Wayzata, MN (US)

(73) Assignee: Apreo Health, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/660,318

(22) Filed: Apr. 22, 2022

(65) Prior Publication Data

US 2022/0241062 A1 Aug. 4, 2022

Related U.S. Application Data

(63) Continuation of application No. 16/902,054, filed on Jun. 15, 2020, which is a continuation of application
(Continued)

(51) Int. Cl.
*A61F 2/04* (2013.01)
*A61F 2/88* (2006.01)
(Continued)

(52) U.S. Cl.
CPC ............ *A61F 2/04* (2013.01); *A61B 18/02* (2013.01); *A61F 2/88* (2013.01); *A61M 29/02* (2013.01);
(Continued)

(58) Field of Classification Search
CPC ........ A61F 2/04; A61F 2/88; A61F 2002/043; A61F 2002/044; A61F 2002/046
See application file for complete search history.

(56) References Cited

U.S. PATENT DOCUMENTS 5,601,593 A 2/1997 Freitag
5,662,713 A 9/1997 Andersen et al.
(Continued)

FOREIGN PATENT DOCUMENTS

AU 2006252347 A1 12/2006
CN 2836753 Y 11/2006
(Continued)

OTHER PUBLICATIONS

International Search Report and Written Opinion dated Dec. 22, 2016, International Application No. PCT/US2016/051512, 9 pages.
(Continued)

*Primary Examiner* — Christopher D. Prone
(74) *Attorney, Agent, or Firm* — Fortem IP LLP; Mary Fox

(57) ABSTRACT

Devices, systems, and methods for improving airflow within an airway. One example embodiment includes a method for treating a subject. The method includes (1) placing an expandable object into one or more airways of the bronchial tree of the subject, (2) expanding the expandable object within at least one of the one or more airways such that at least a portion of a wall of the one or more airways is expanded, and (3) placing a stent in the airway such that a portion of the stent is adjacent to the portion of the wall of the one or more expanded airways.

21 Claims, 16 Drawing Sheets

Related U.S. Application Data

No. 15/409,875, filed on Jan. 19, 2017, now Pat. No. 10,682,218, which is a continuation of application No. 14/852,609, filed on Sep. 13, 2015, now Pat. No. 9,592,138.

(51) Int. Cl.
*A61M 29/02* (2006.01)
*A61B 18/02* (2006.01)
*A61B 18/00* (2006.01)
*A61F 2/958* (2013.01)

(52) U.S. Cl.
CPC .............. *A61B 2018/0022* (2013.01); *A61B 2018/0212* (2013.01); *A61F 2/958* (2013.01); *A61F 2002/043* (2013.01); *A61F 2250/0048* (2013.01); *A61F 2250/0067* (2013.01)

(56) References Cited

U.S. PATENT DOCUMENTS

| | | | |
|---|---|---|---|
| 6,019,779 | A | 2/2000 | Thorud et al. |
| 6,071,305 | A | 6/2000 | Brown et al. |
| 6,241,718 | B1 | 6/2001 | Arless et al. |
| 6,514,290 | B1* | 2/2003 | Loomas ............... A61F 2/0063 606/232 |
| 6,527,761 | B1 | 3/2003 | Soltesz et al. |
| 6,575,933 | B1 | 6/2003 | Wittenberger et al. |
| 7,422,584 | B2 | 9/2008 | Loomas et al. |
| 7,426,929 | B2 | 9/2008 | Tanaka |
| 7,462,162 | B2 | 12/2008 | Phan et al. |
| 7,556,624 | B2 | 7/2009 | Laufer et al. |
| 7,670,373 | B1 | 3/2010 | Sabanathan |
| 8,092,549 | B2 | 1/2012 | Hillis et al. |
| 9,592,138 | B1 | 3/2017 | Mayse |
| 10,682,218 | B2 | 6/2020 | Mayse |
| 2001/0037808 | A1* | 11/2001 | Deem ............... A61F 2/91 128/200.24 |
| 2002/0042565 | A1 | 4/2002 | Cooper et al. |
| 2003/0024527 | A1* | 2/2003 | Ginn ............... A61M 16/0406 128/200.24 |
| 2005/0056292 | A1 | 3/2005 | Cooper |
| 2005/0096529 | A1 | 5/2005 | Cooper et al. |
| 2006/0074396 | A1 | 4/2006 | Stiger |
| 2006/0106455 | A1 | 5/2006 | Furst et al. |
| 2006/0135947 | A1 | 6/2006 | Soltesz et al. |
| 2007/0250148 | A1 | 10/2007 | Perry et al. |
| 2008/0132988 | A1 | 6/2008 | Jordan |
| 2009/0182273 | A1 | 7/2009 | Johnson |
| 2010/0122698 | A1 | 5/2010 | Shaffer et al. |
| 2010/0286760 | A1 | 11/2010 | Beach et al. |
| 2011/0040371 | A1 | 2/2011 | Hanssen et al. |
| 2012/0316559 | A1 | 12/2012 | Mayse et al. |
| 2013/0103163 | A1* | 4/2013 | Krimsky ............... A61F 2/90 623/23.65 |
| 2015/0025629 | A1* | 1/2015 | Weber ............... A61F 2/04 623/9 |
| 2016/0338822 | A1 | 11/2016 | Rocha |
| 2016/0374689 | A1* | 12/2016 | Tanaka ............. A61B 17/00491 606/191 |
| 2017/0071765 | A1 | 3/2017 | Mayse |
| 2017/0128186 | A1 | 5/2017 | Mayse |
| 2017/0245977 | A1 | 8/2017 | Foster et al. |
| 2017/0281378 | A1 | 10/2017 | Shintaku et al. |
| 2022/0280279 | A1 | 9/2022 | Mayse |

FOREIGN PATENT DOCUMENTS

| | | |
|---|---|---|
| EP | 3095414 A1 | 11/2016 |
| JP | 2003506132 A | 2/2003 |
| JP | 2011036272 A | 2/2011 |
| WO | 2012103501 A1 | 8/2012 |
| WO | 2012128032 A1 | 9/2012 |
| WO | 2014143898 A1 | 9/2014 |

OTHER PUBLICATIONS

Takahashi et al., "Ultraflex Expandable Stents for the Management for Air Leaks", Annals of Thoracic and Cardiovascular Surgery, 2006年02月, vol. 12, No. 1, pp. 50-52, ISSN:1341-1098.

* cited by examiner

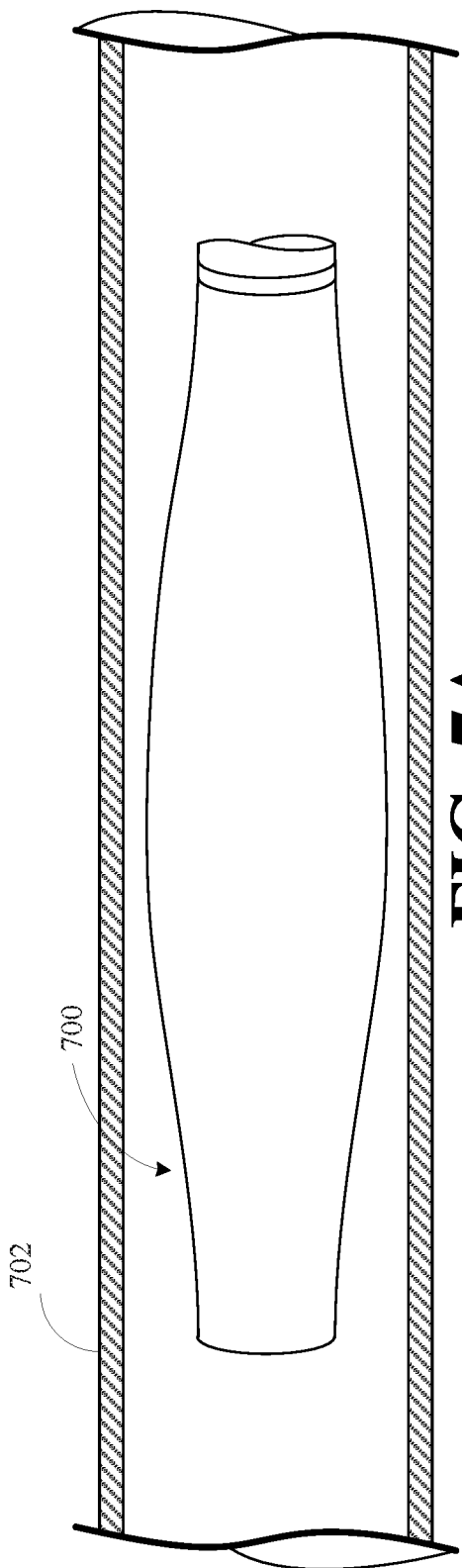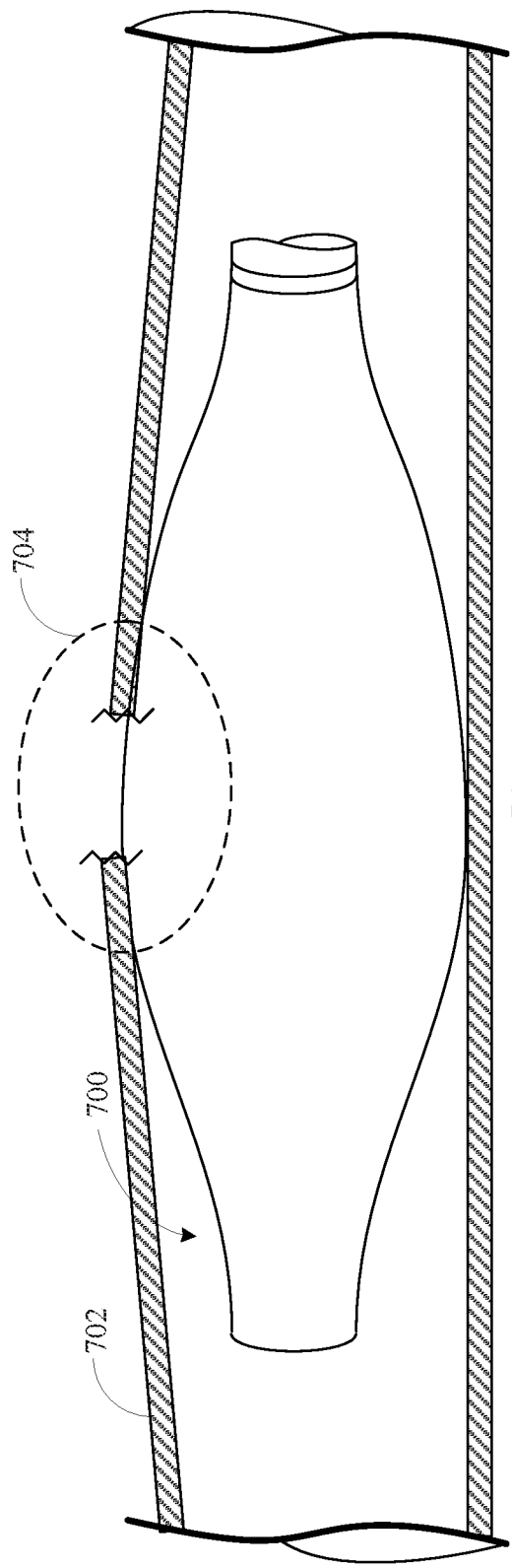

DEVICES, SYSTEMS, AND METHODS FOR TREATING PULMONARY DISEASE

CROSS-REFERENCE TO RELATED APPLICATIONS

This application is a continuation of U.S. patent application Ser. No. 16/902,054, filed Jun. 15, 2020, which is a continuation of U.S. patent application Ser. No. 15/409,875, filed Jan. 19, 2017, no U.S. Pat. No. 10,682,218, which is a continuation of U.S. patent application Ser. No. 14/852,609, filed Sep. 13, 2015, now U.S. Pat. No. 9,592,138, which are incorporated herein by reference in their entireties.

BACKGROUND

Obstructive lung disease, including emphysema, chronic bronchitis, asthma and others, may lead to various obstructions and/or narrowing of airways within the bronchial tree. Airways that are affected by obstructive lung disease may include, for example, any of the trachea, main bronchi, lobar bronchi, segmental bronchi, sub-segmental bronchi, bronchioles, conducting bronchioles, terminal bronchioles and respiratory bronchioles. Airway obstructions may include the formation of mucous in the airways and/or scaring of the airways. Airway narrowing may be characterized by loss of radial tension of airways, thickening of the airway wall, and/or bronchoconstriction, among other examples. Further, obstructive lung disease may lead to breakdown of alveolar walls.

It becomes increasingly difficult for a patient to exhale as the airways or alveoli become damaged. Patients afflicted by obstructive lung disease may also face loss in muscle strength and an inability to perform common daily activities, among other ill effects. More detailed aspects of obstructive lung disease including additional aspects of the lungs, the bronchial tree, and airways are discussed further below.

There have been many attempts to cure and/or improve damage of the bronchial tree caused by obstructive lung disease. Other attempts have been made to relieve the obstruction and/or narrowing caused by obstructive lung disease. Still other attempts have been made to improve airflow into and out of the alveoli of a lung. However, these attempts have so far been met by many challenges.

Some treatments involve placement of a prosthetic, such as a conventional stent, in the central airways (i.e., the trachea, main bronchi, lobar bronchi, and/or segmental bronchi) in an attempt to maintain patency of these airways. Unfortunately, the central airways only contribute a portion of the overall airway obstruction and/or airway narrowing seen in patients with obstructive lung disease. Further, prosthetics, when placed in the bronchial airways, are plagued by issues of occlusion including the formation of granulation tissue and mucous impaction. Accordingly, treatments that involve the placement of conventional stents in airways often result in only short term improved outcomes for patients because the stent is eventually occluded.

Other treatments involve attempts to bypass an obstructed bronchial airway by forming a perforation through the chest wall into the outer portions of the lung, thereby creating a direct communication (i.e., bypass tracts) between diseased alveoli and outside of the body. If no other steps are taken, these bypass tracts will close by normal healing or by the formation of granulation tissue. Treating physicians may attempt to extend the duration of patency by placing a tubular hollow prosthetic in the bypass tract. However, such prosthetics can induce a foreign body reaction and accelerate the formation of granulation tissue, thereby causing the bypass tracts to eventually become occluded. Moreover, such a bypass procedure is difficult to perform, is time intensive, and is uncomfortable, inconvenient, and debilitating for the patient.

Yet other treatments involve forming a perforation between select central airways such as the main bronchi or lobar bronchi and the diseased alveoli in an attempt to bypass the obstructed connecting airways. If no other steps are taken, the perforations regularly heal closed, minimizing the long-term effectiveness of such treatments. Attempts have been made to maintain patency of the perforation by placing supporting stents in the lumen of the perforation. Additionally, the stents may be covered with silicone and/or coated with antiproliferative drugs to minimize the effect of the normal healing response and/or the foreign body reaction including granulation tissue formation. Unfortunately, however, these measures are typically inadequate and the supporting stents again induce a foreign body reaction including granulation tissue formation that often occludes the stent and results in closure of the perforation. Additionally, mucous produced from glands in the central airways often occludes the stent and results in closure of the perforation.

These and other problems continue to plague existing treatments for obstructive lung disease, and no reliable way to avoid such problems has yet been developed. It would therefore be desirable to develop treatments for issues caused by obstructive lung disease—including as examples obstruction and narrowing of airways of the bronchial tree—that more reliably avoid the problems encountered by existing treatments.

SUMMARY

This disclosure includes various devices, systems, and methods useful for improving airflow within a bronchial tree and/or into and out of the alveoli of the lung. In some examples, the airways that connect central airways to alveoli are enlarged so as to improve airflow between the central airways and the alveoli. In some cases, the connecting airways that connect the central airways to alveoli may be enlarged beyond their normal size to further improve airflow. In still other cases, when the airways are enlarged beyond their normal size, the walls of some of the airways may become perforated allowing communication of additional alveoli that are adjacent to the connecting airways with the central airways.

A first aspect of the disclosure involves an open form stent that, when placed within a lung of a patient, generally facilitates airflow to and/or from particular alveoli and more central airways, and also facilitates a minimization and localization of the formation of granulation tissue. Beneficially, the open form stent of the first aspect also makes use of collateral airflow between the particular alveoli and surrounding alveoli that is normally present in a lung, that is accentuated in an obstructed lung, and that is further accentuated in an emphysematous lung. In particular, because the open form stent improves airflow between the particular alveoli and more central airways, more of the collateral airflow is able to make its way to the central airways as well.

A second aspect of the disclosure involves an expandable object that, when placed within a lung of a patient, may expand one or more airway(s) beyond their normal diameter. Expansion of an airway may cause perforation(s) or tear(s) in the wall of the airway, thereby creating direct communications between the airway and surrounding alveoli, and may thereby increase airflow in and out of the airway not only from the alveoli normally connected to the airway but also from alveoli surrounding the airway. In one example the expandable object is a dilatory balloon. In another example the expandable object is a dilatory cryo balloon. In another example the expandable object is a wire basket. In another example the expandable object is the open form stent. Other examples exist.

A third aspect of the disclosure involves a method for treating a patient using a stent (in some examples, an open-form stent) and an expandable object. According to such a method, the expandable object may be used to expand one or more obstructed airways and/or cause perforation(s) or tear(s) (i.e., openings) in the wall of the airway, and then the stent may be placed within the airway to further facilitate airflow within the airway. The stent may be placed for an indefinite period of time, or may be removed after a given period of time.

In some examples, a stent may be used to improve airflow without use of an expandable object. In other examples, an expandable object may be used to improve airflow without use of a stent.

As discussed in more detail below, this disclosure involves other aspects as well, some of which include and/or incorporate the three aspects mentioned above.

One example embodiment includes a method for treating a subject. The method includes (1) placing an expandable object into one or more airways of the bronchial tree of the subject, (2) expanding the expandable object within at least one of the one or more airways such that at least a portion of the wall of the one or more airways is expanded, and (3) placing a stent in the one or more airways such that a portion of the stent is adjacent to the portion of the wall of the one or more expanded airways. In some examples, the method involves (1) placing an expandable object into two or more airways of the bronchial tree of the subject, where a first end of the expandable object is situated within a first airway of the bronchial tree and a second end of the expandable object is situated within a second airway of the bronchial tree, (2) expanding the expandable object within at least two of the two or more airways such that at least a portion of a wall of the two or more airways is expanded, and (3) placing a stent within the at least two of the two or more airways such that a portion of the stent is adjacent to the portion of the wall of the two or more expanded airways.

Another example embodiment includes a system used for treating a subject. The system includes (1) an expandable object, (2) a stent, and (3) instructions for improving airflow in one or more airways of a bronchial tree of a subject using the expandable object and the stent. The instructions for improving airflow in the airway of the bronchial tree of the subject using the expandable object and the stent may include, in one example: (a) placing an expandable object into one or more airways of the bronchial tree of the subject, (b) expanding the expandable object within at least one of the one or more airways such that at least a portion of the wall of the one or more airways is expanded, and (c) placing a stent in the one or more airways such that a portion of the stent is adjacent to the portion of the wall of the one or more expanded airways.

These as well as other embodiments, aspects, advantages, and alternatives will become apparent to those of ordinary skill in the art by reading the following detailed description, with reference where appropriate to the accompanying drawings.

BRIEF DESCRIPTION OF THE DRAWINGS

FIGS. 7A and 7B show aspects of an expandable object within an airway.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that aspects of the present disclosure, as generally described herein, and illustrated in the figures, can be arranged, substituted, combined, separated, and/or designed in a wide variety of different configurations, all of which are contemplated herein.

The devices, systems, and methods described herein may be used for the purpose of improving airflow within a bronchial tree. More particularly, some devices, systems, and methods described herein include stents and expandable objects that may be used to improve airflow in airways of a patient's bronchial tree. However, it should be understood that such an application is but one particular application of the devices, systems, and methods described herein, and that other applications are certainly possible as well.

The devices, systems, and methods described herein may generally provide for improved airflow in a manner that is relatively efficient, effective, and redundant when compared to other techniques. As one example, the devices, systems, and method described herein may minimize granulation and/or minimize occlusion issues associated with other known techniques that involve the use of foreign bodies. The devices, systems, and method described herein may also avoid some discomfort and inconvenience associated with some known techniques that involve the use of bypass paths. Therefore, many of the disadvantages of other techniques directed at attempts to improve airflow may be avoided.

1. EXAMPLE PATIENT

Figure 1:
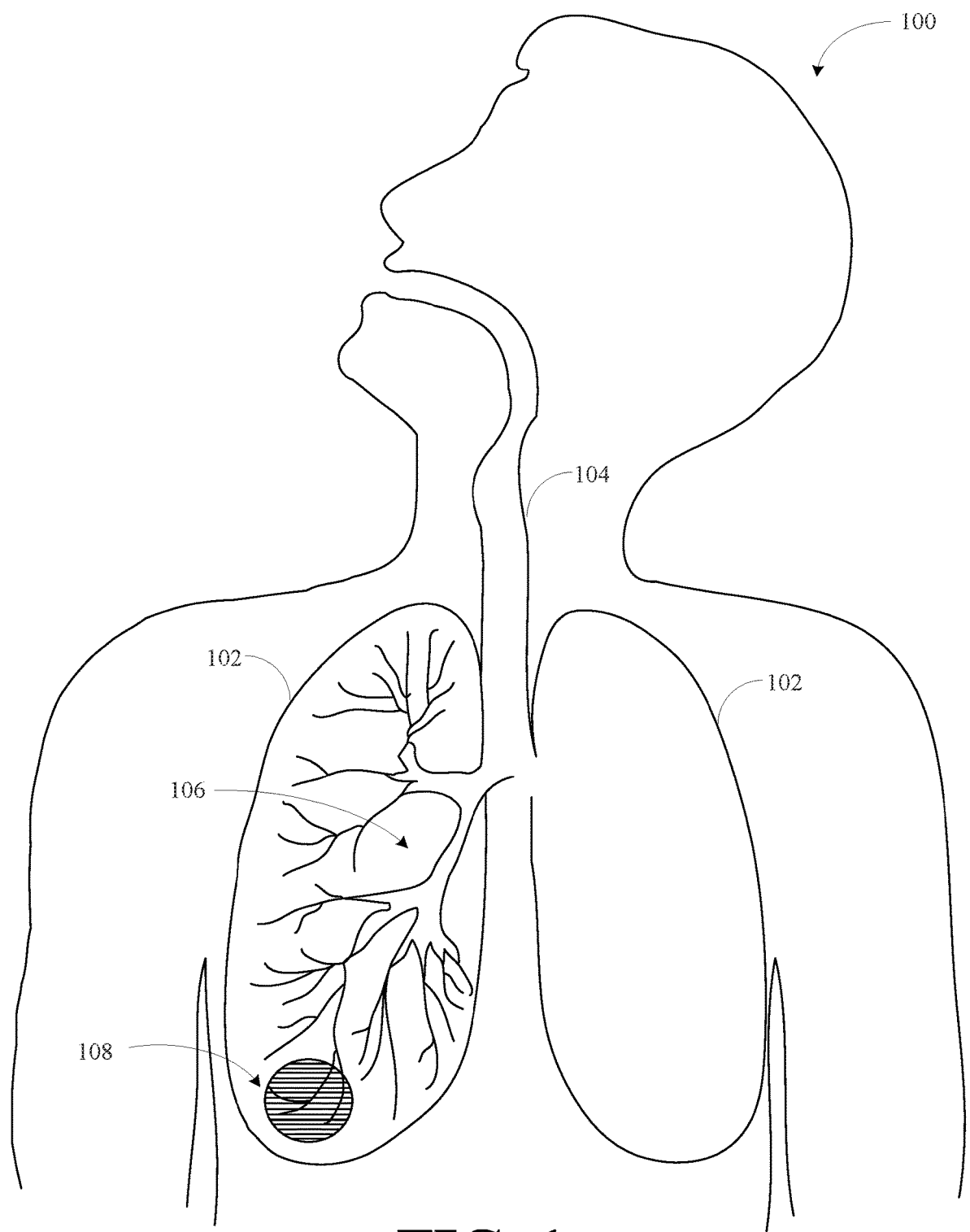
FIG. 1 shows aspects of an example patient.

For purposes of example and explanation, FIG. 1 shows aspects of an example patient 100. As shown, within patient 100 are lungs 102. Lungs 102 may generally be accessed by a treating physician via the patient's trachea 104, perhaps using a bronchoscope, catheter, or other such delivery device introduced to the patient's trachea through the mouth or nose.

The patient's lungs contain a portion of the patient's bronchial tree 106. Bronchial tree 106 includes numerous airways including central airways such as the right and left main bronchus and the lobar bronchi, intermediary airways such as numerous segmental and sub-segmental bronchi, and non-central periphery airways such as the bronchioles, conducting bronchioles, terminal bronchioles and respiratory bronchioles., etc., discussed further below.

The example bronchial tree shown also includes a diseased portion 108 located at a terminal point of the bronchial tree. In some example situations, diseased portion 108 may be understood to be affected by an obstructive lung disease such as emphysema, among other examples.

The diseased portion may be characterized by damage that impairs the passage of air between airways and the alveoli, and therefore ultimately impairs the passage of gas from the air outside the patient to/from the lungs to/from the patient's blood stream. For example, certain airways within the diseased portion may be occluded, collapsed, and/or otherwise constricted. At the same time, alveolar walls within alveoli of the diseased portion may have deteriorated.

To more fully understand the detrimental effects of obstructive lung disease, a cursory discussion of the workings of the lungs may be beneficial. One function of the lungs is to permit the exchange of two gasses by removing carbon dioxide from blood and replacing it with oxygen. To facilitate this gaseous exchange, the lungs move oxygen and carbon dioxide between the air outside the patient's body and blood by bulk conduction through the bronchial tree to the alveoli and diffusion across a blood gas interface within the patient's alveoli.

The air is brought to the patient's alveoli via airways of the patient's bronchial tree, housed within the patient's lungs. The bronchial tree includes branching airways that become narrower, shorter, and more numerous as they penetrate deeper into the lung. As noted above, the trachea branches into the right and left main bronchus, which divide into a multitude of conducting airways starting with the lobar bronchi, intermediary airways such as segmental and sub-segmental bronchi, and periphery airways such as the bronchioles, conducting bronchioles, and finally terminal bronchioles.

Figure 2:
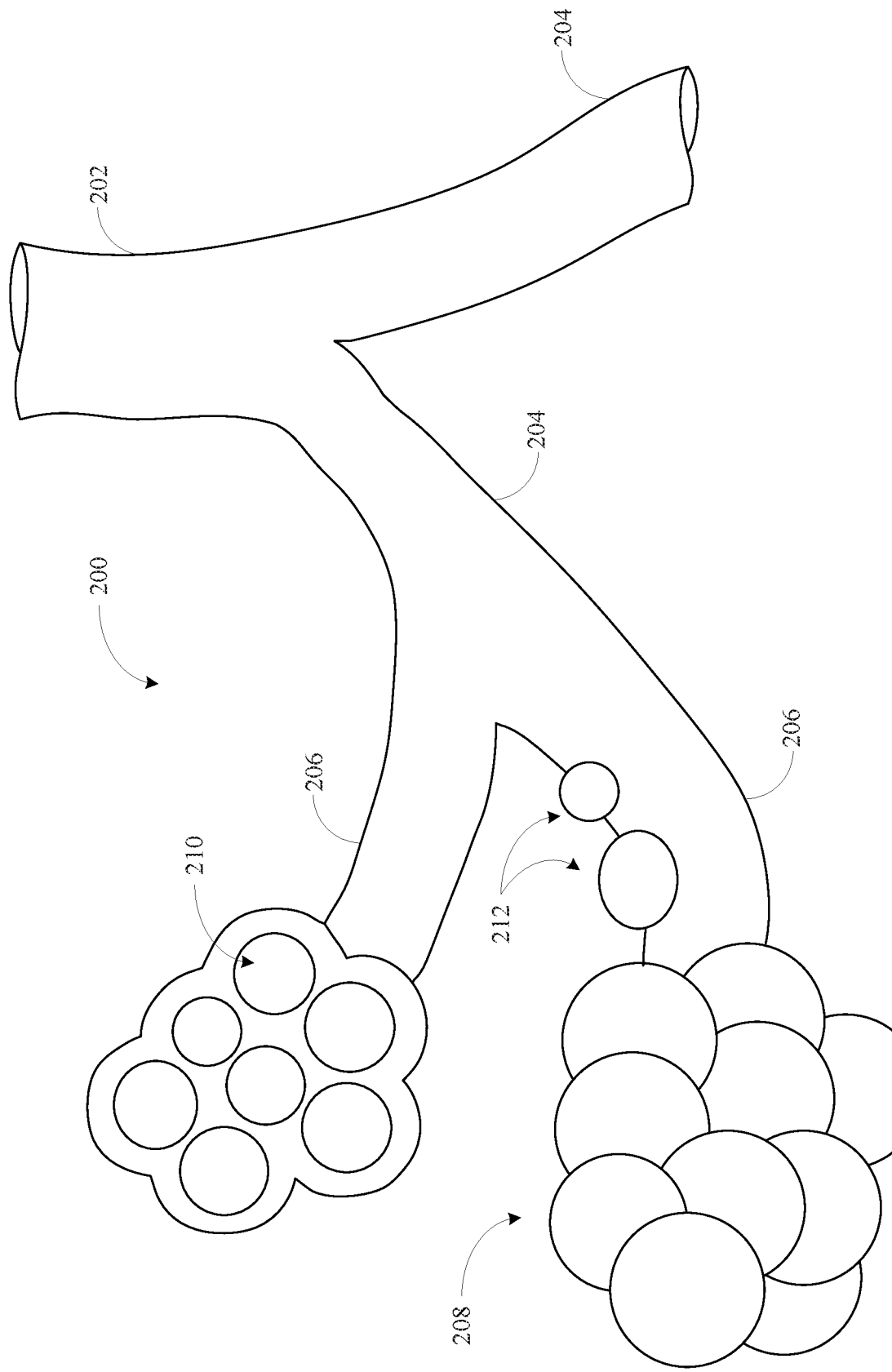
FIG. 2 shows aspects of a terminal portion of an example bronchial tree.

The terminal bronchioles each gives rise to several respiratory bronchioles, which go on to divide into multiple alveolar ducts, often ranging in number from two to eleven. FIG. 2 shows aspects of the terminal portion of the example bronchial tree, including examples of such smaller bronchioles.

Example bronchial tree 200 includes bronchiole 202, which divides into terminal bronchioles 204. Terminal bronchiole 204 then divides into respiratory bronchioles 206. Also shown are example alveoli 208, containing alveolar sacs 210. As shown, various alveoli 212 may be present along the length of a respiratory bronchiole 206 as well.

The terminal bronchioles 204 are the smallest airways that do not contain alveoli. A function of the bronchi and bronchioles is to provide conducting airways that lead air to and from the alveoli. However, the conducting airways do not contain alveoli and do not take park in gas exchange. Rather, gas exchange takes place in the alveoli that are found distal to the conducting airways, starting at the respiratory bronchioles.

It is common to refer to, or otherwise characterize, the various airways of the bronchial tree according to "generations." For instance, the trachea is referred to as "generation 0" of the bronchial tree. Various levels of bronchi, including the left and right main bronchi, are referred to as "generation 1." The lobar bronchi are referred to as "generation 2." The segmental bronchi are referred to as "generation 3." Various bronchioles are referred to "generation 4 though 19." Terminal bronchioles, for instance, are approximately "generation 14-18." Respiratory bronchioles, for instance, are approximately "generation 16-20." Further, it is common to refer to the airways extending from the trachea to the terminal bronchi as "conducting airways."

Obstructive lung disease, such as emphysema in particular, is characterized by irreversible destruction of the alveolar walls that contain elastic fibers that maintain radial outward traction on small airways and are useful in inhalation and exhalation. When these elastic fibers are damaged, these small airways are no longer under radial outward traction and can collapse, particularly during exhalation. As such, when these fibers are damaged, air may be trapped in the lungs and not be able to be completely expelled during exhalation. Emphysema results in hyperinflation (air trapping) of the lung and an inability of the person to exhale. In this situation, the individual will be debilitated since the lungs are unable to perform gas exchange at a satisfactory rate and the lungs are hyperinflated and applying pressure to the chest wall, diaphragm, and surrounding structures.

One further aspect of alveolar wall destruction is that the airflow between neighboring air sacs, known as collateral ventilation or collateral air flow, is increased. However, this alone is of little or no benefit to the patient because air is still unable to flow into and out of the lungs through the collapsed and obstructed airways.

Chronic bronchitis is characterized by excessive mucous production in the bronchial tree. Usually there is a general increase in bulk (hypertrophy) of the large bronchi and chronic inflammatory changes in the small airways. Excessive amounts of mucus are found in the airways and semi-solid plugs of the mucus may occlude small bronchi. Also, the small airways are usually narrowed and show inflammatory changes.

The devices, systems, and methods described herein may generally be used to improve airflow out of hyperinflated alveoli within a diseased portion 108 of the lung that are affected by obstructive lung disease such as emphysema and/or bronchitis and into central airways of the bronchial tree. Accordingly, the example stents and expandable objects described more fully below may be delivered to and placed within airways that connect central airways to the distal airways and alveoli of diseased portion 108.

2. EXAMPLE OPEN-FORM STENT

Figure 3A:
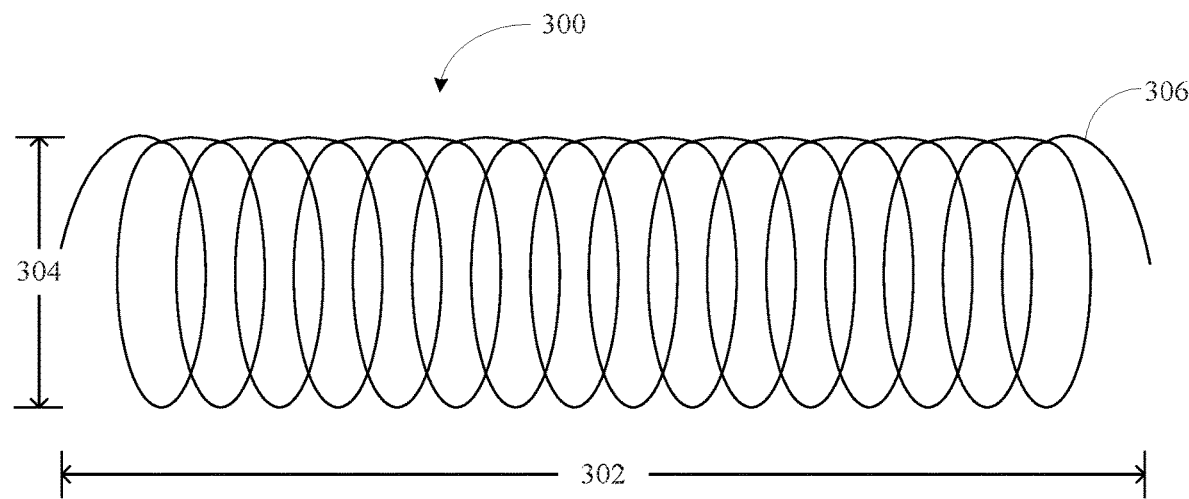
FIG. 3A shows aspects of an example open-form stent.

FIG. 3A shows aspects of an example open-form stent 300. As shown the open-form stent may generally have an open configuration, in the form of a coil-like or spring-like structure. It may be understood that the coil is characterized by a continuous outer diameter. Herein, the outer diameter of the coil may sometimes be referred to as an "open-form wall" for purposes of example and explanation. As a result of the open-form configuration of the stent, it will be appreciated that no portion of the open-form stent entirely isolates a given area of the open-form wall. In other words, the open-form wall comprises a continuously open helical surface, discussed further below in connection with FIGS. 4A and 4B.

Figure 3B:
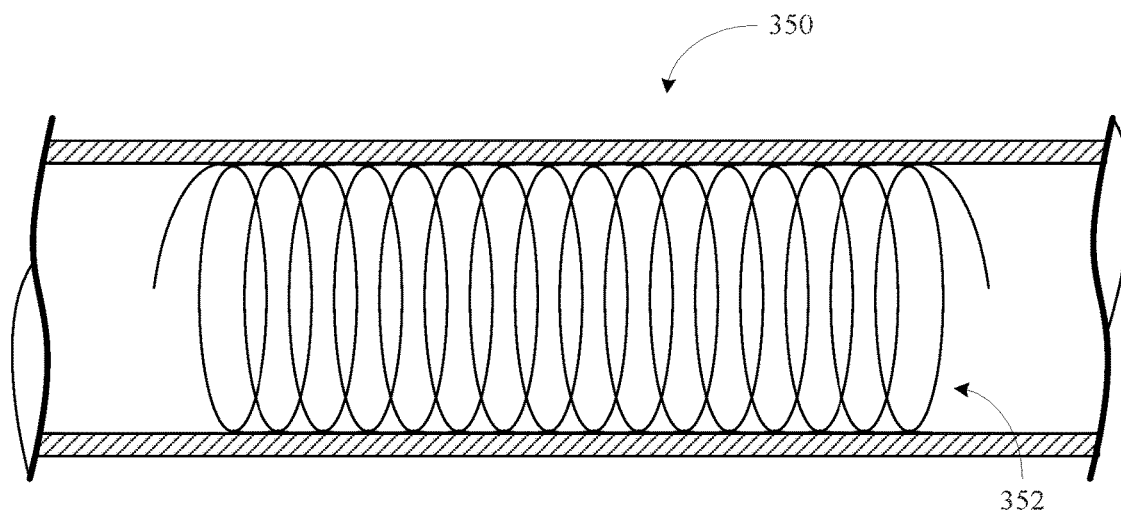
FIG. 3B shows aspects of an example open-form stent within an airway.

FIG. 3B shows aspects of open-form stent 352 in airway 350. Those of skill in the art will appreciate that surface of airway 350 may be characterized by a mucociliary structure (or "elevator") on its inner wall that is capable of clearing mucous within the airway. The mucociliary structure may include cilia that continuously move mucous along, and ultimately out of, the airway. Because no portion of open-form stent 350 entirely isolates a given area of the inner wall of airway 350, natural mucociliary processes of the airway may generally not be inhibited when the open-form stent is in place.

As discussed further below with respect to FIGS. 4C and 4D, traditional closed-form stents interrupt the function of the mucociliary structure by preventing exposure of the mucous to the mucociliary structure altogether and/or closing off a given area of the airway wall so that mucous may not advance further along the airway. However, the open-form stent shown in FIGS. 3A and 3B allows exposure of the airway wall to the inside of the airway even when the stent is in place, and also does not totally block the mucociliary structure in any one direction. As such, even when the open-form stent is in place, the mucociliary structure may continue to facilitate mucuous clearance along a helical pathway that runs through the center of the coil.

As another advantage, the open-form stent may be characterized by a certain amount of flexibility and recoil, such that the open-form stent will minimize mechanical toxicity within the airway, especially when expanding across multiple airways. Given the flexibility of the open-form stent, it may bend and move with the airway, and thereby minimize foreign-body response within the airway. As a result, such an open-form stent will minimize inflammation and will minimize the formation of granulation tissue within the airway. Further, what inflammation and granulation tissue that forms will be concentrated near the contact of the stent with the wall such that air and/or mucous may still move along the airway in the helical open space of the stent.

As yet another advantage, because the open-form stent is characterized by an open-form wall that does not close off the exterior of the stent from the interior of the stent, the open-form stent may allow for collateral airflow from side passages, such as alveoli or induced perforations connecting to other surround alveoli, into the main lumen of the airway.

The open-form stent may be formed of any suitable material. For instance, the open-form stent may be formed of a silicone polyester material. Examples include urethane, polyethylene terephthalate (PET), polytetrafluoroethylene (PTFE), and polyetherether ketone (PEEK). In other cases, the open-form stent may be formed of a metal material. Examples include stainless steel and nitinol. Other examples of suitable materials exist.

The open-form stent may be coated in one or more suitable coatings. In one example, the open-form stent may be coated in an antiproliferative agent such as sirolimus, everolimus, zotarolimus, paclitaxel, taxotere, mitomycin-C, among others. In another example, the open-form stent may be coated in an antimucous agent such as atropine, ipratropium, tiotropium or a steroid. In yet another example, the open form stent may be coated in a mucolytic material such as N-acetylcystine or guaifenesin. In yet another example still, the open-form stent may be coated in a hydrophilic material. Other examples of suitable coatings exist.

As shown in FIG. 3A, example open-form stent 300 has a given length 302, which may be any suitable length and may vary depending on application including what airway(s) the open-form stent is to ultimately be placed. In one example, length 302 may be between 2 cm to 10 cm in length. For instance, length 302 may be approximately 6 cm in length. Other lengths may be suitable as well.

As also shown in FIG. 3A, example open-form stent 300 has a given height, or diameter 304, which may be any suitable diameter and may vary depending on application including what airway(s) the open-form stent is to ultimately be placed. In one example, diameter 304 may be between 1 mm to 10 mm. For instance, the diameter may be between 4 mm to 8 mm. In other cases, the diameter may be approximately 6 mm. Other diameters may be suitable as well.

Further, example open-form stent 300 may include a hook 306 on one or both ends. The hook may be looped back on itself so as to form a closed structure at one or both ends. Alternatively and/or additionally, the open-form stent 300 may include a smooth, rounded ball at one or both ends. Such structures as the hook, loop, or ball may be used when placing the open-form stent in an airway, to aid the accessibility and/or manipulability of the open-form stent. Use of such structures may further limit the trauma the ends of the open-stent may cause on tissue. For example, such a structure may further limit the formation of granulation tissue or may prevent formation of a pneumothorax if an end of the open-form stent were to come into contact with the visceral pleura, and/or may prevent pain if an end of the open-form stent were to come into direct or indirect contact with the parietal pleura.

Figure 4A:
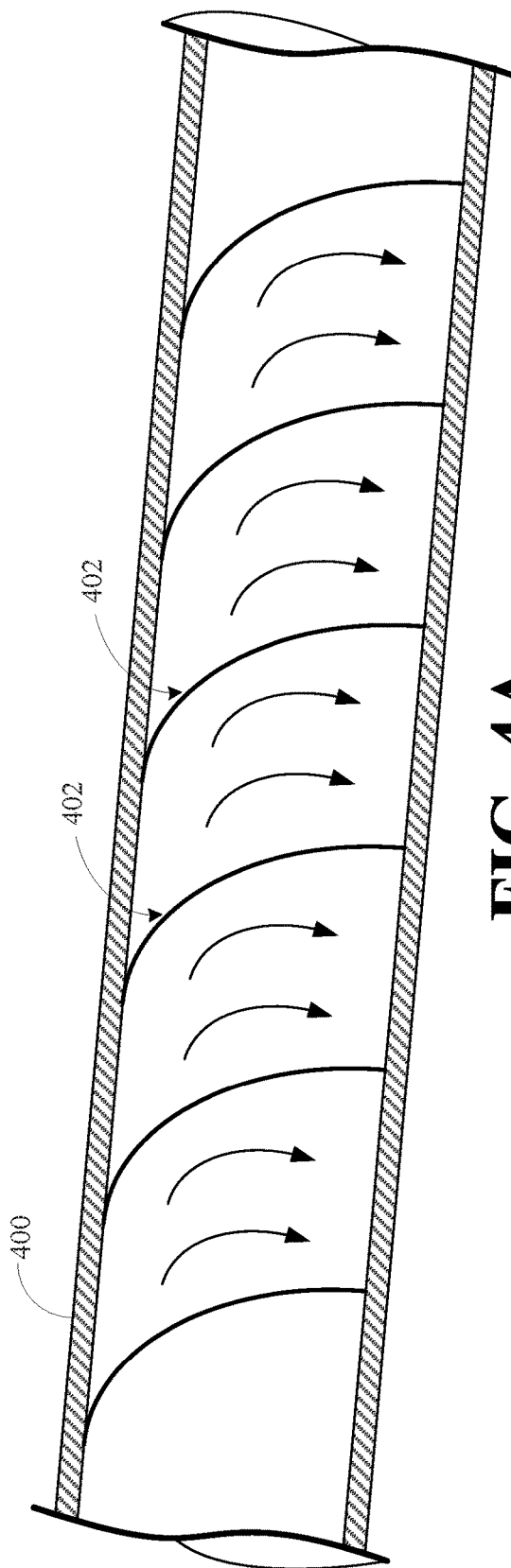
FIGS. 4A and 4B show aspects of an airway having an example open-form stent placed within the airway.

FIG. 4A shows aspects of open-form stent 402 within airway 400. Also depicted in FIG. 4A is a continuous helical pathway along the wall of airway 400 that remains when open-form stent 402 is placed within airway 400. As shown by the various arrows in FIG. 4A, a continuous helical pathway exists along the open-form wall of the open-form stent that permits relatively uninterrupted traversal of the inner wall of the airway along the helical pathway. As noted above, mucouos may be cleared along this helical pathway by the mucociliary structure of airway 400. Of note, although open-form stent 402 is shown within only a single portion of airway 400, it should be understood that open-form stent 402 may extend into other portions of airway 400 and/or may extend into other airways altogether.

Figure 4B:
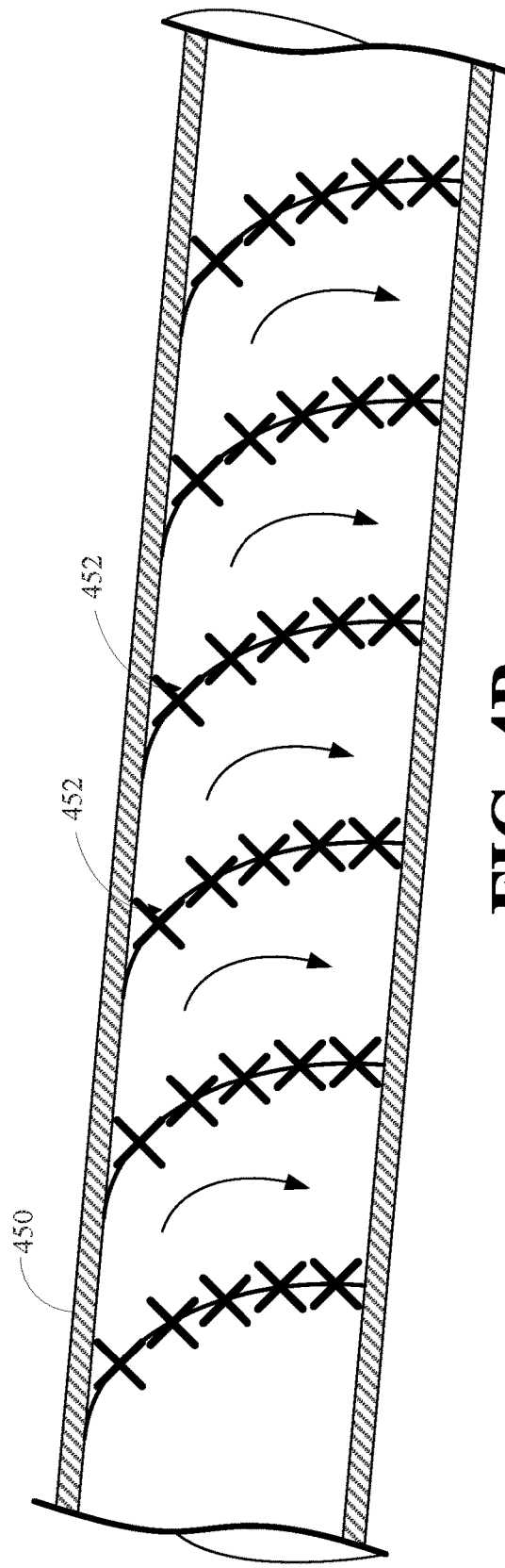

FIG. 4B shows aspects of open-form stent 452 within airway 450. Like open-form stent 402, open form-form stent 452 is characterized by a continuous helical pathway that exists along its open-form wall. Also depicted in FIG. 4B is granulation tissue along the structure of open-form stent 452, shown as various X indicators along the open-form stent. As shown, the granulation tissue formation is localized along the structure of the open-form stent itself. As a result, the continuous helical pathway along the open-form wall remains. Thus, despite the formation of granulation tissue, the mucociliary structure of airway 450 is not prevented from functioning to clear mucous from the airway and an uninterrupted pathway for the movement of air along the airway remains.

Figure 4C:
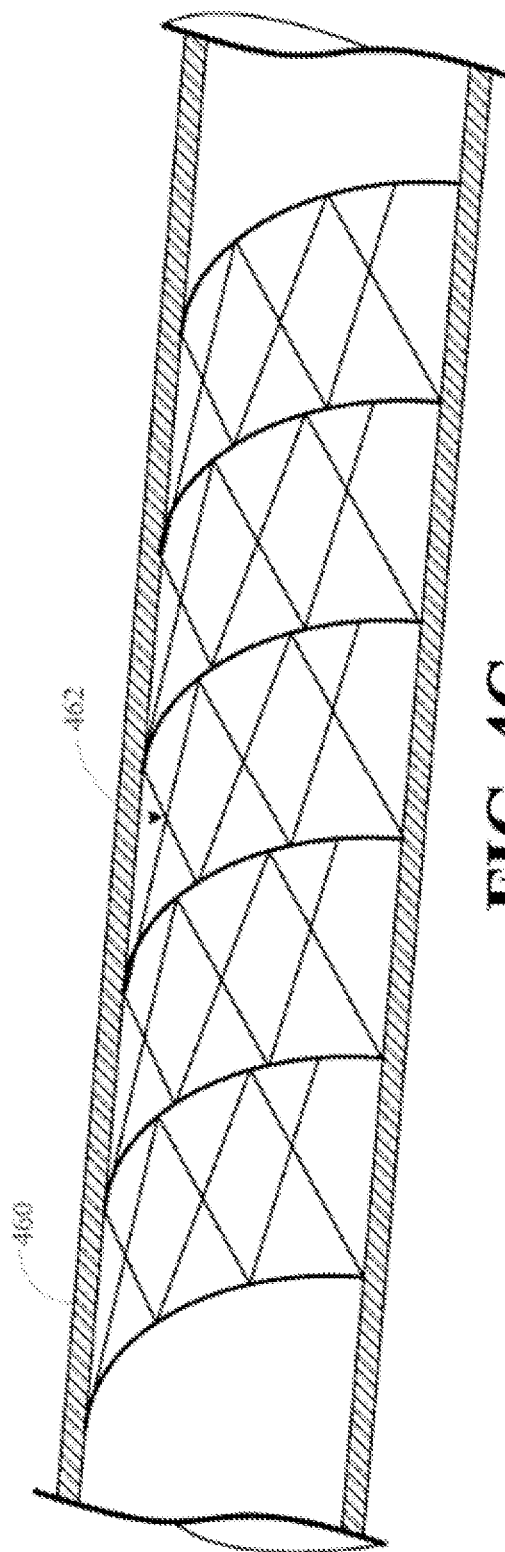
FIGS. 4C and 4D show aspects of an airway having an example closed-form stent placed within the airway.

FIG. 4C shows aspects of closed-form stent 462 within airway 460, as known in the art. In contrast to the example open-form stent as shown in FIGS. 4A and 4B, closed-form stent 462 does not provide a continuous helical pathway along the wall of airway 460. Instead, the structure of closed-form stent 462, including its pervasive structure along its length, prevents traversal of the inner wall of the airway. While a particular example structure is shown in FIG. 4C as a closed-form wire frame, those of skill in the art will appreciate that other known closed-form stents exist including stents characterized by solid (rather than wireframe) walls.

Figure 4D:
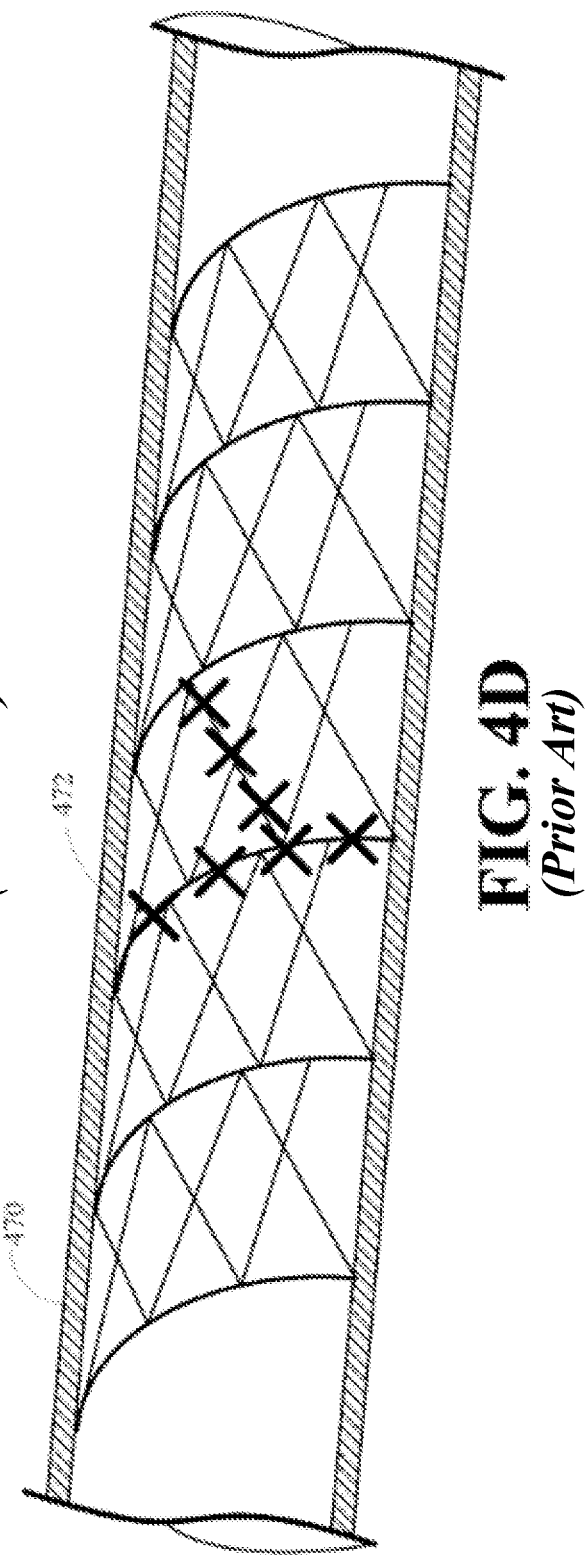

FIG. 4D shows aspects of closed-form stent 472 within airway 470. Like closed-form stent 462, closed-form stent 472 does not provide a continuous helical pathway along the wall of airway 470. Also depicted in FIG. 4D is granulation tissue along the structure of closed-form stent 472, shown as various X indicators along the closed-form stent (representative granulation tissue not shown along all structure of the closed-form stent). As shown, the granulation tissue formation is localized along the structure of the closed-form stent, but because the closed-form stent includes pervasive structure along its length, the granulation tissue formation is also pervasive along the length of the closed-form stent. Thus, unlike in the case of the open-form stent shown in FIGS. 4A and 4B, the formation of granulation tissue along closed-form stent 472 further prevents the mucociliary structure of airway 470 from functioning to clear mucuous from the airway.

Figure 5A:
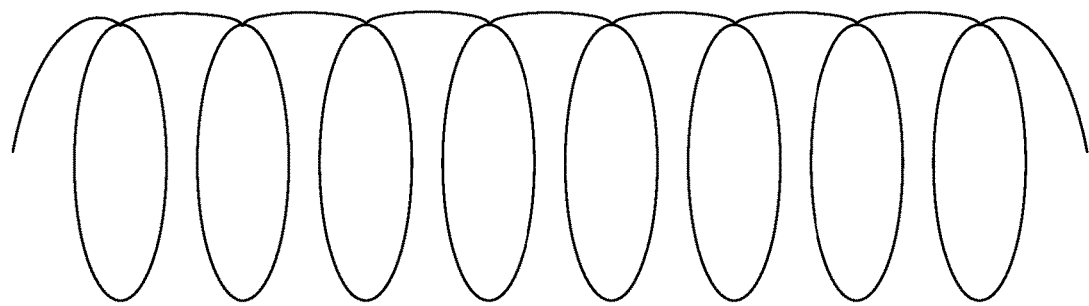
FIGS. 5A and 5B show aspects of an example open-form stent.
Figure 5B:
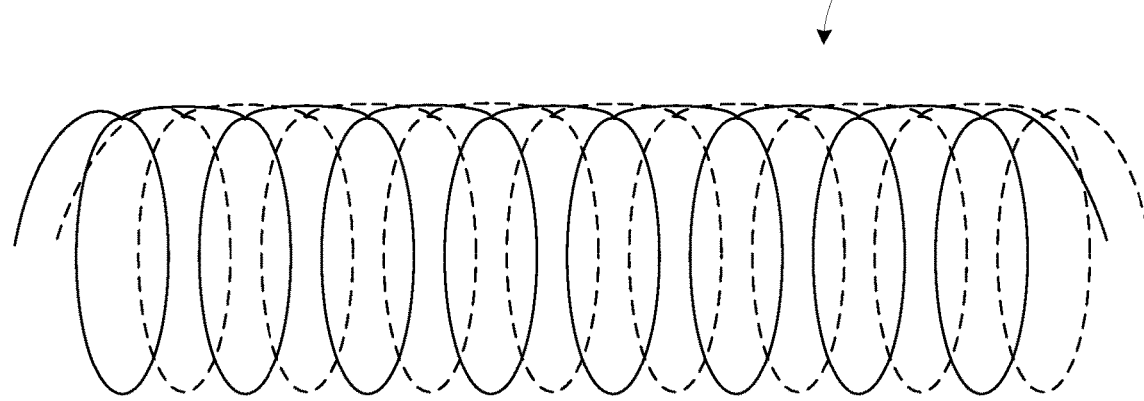
Figure 5C:
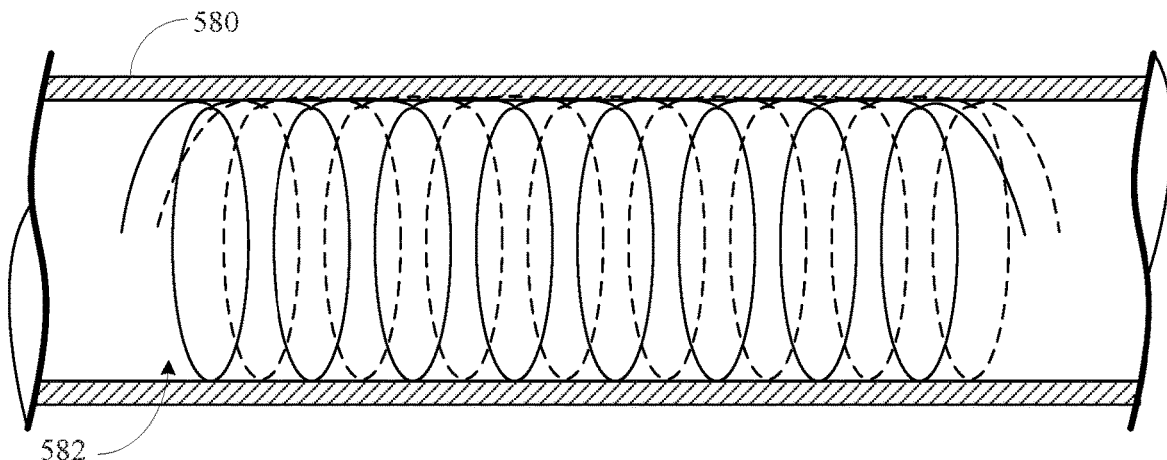
FIG. 5C shows aspects of an example open-form stent within an airway.

FIGS. 5A-5C show an alternative example open-form stent. FIG. 5A shows an example open-form stent 500, characterized by relatively less turns per unit length than that shown above with respect to FIGS. 3A and 3B. In one implementation, the coil structure of open-form stent 500 may be combined with at least one additional coil structure to form an open-form stent that is characterized by at least a double helix structure.

An example of an example double helix open-form stent 550 is shown in FIG. 5B. As shown, example open-form stent is formed of a first coil structure 552 and a second coil structure 554. In some embodiments, the first coil structure 552 and the second coil structure 554 may connect at one or both ends of the open-form stent thereby creating a loop. Such a loop may aid in placement or removal and may also eliminate any potential sharp ends of the first coil 552 and the second coil 554 thereby decreasing trauma that the open form stent may cause to the airway and surrounding tissues. This double coil open-form stent can produce the same area of stent-airway wall contact as a single coil open-form stent, but produce less angulation of the coil wires relative to the airway compared to that which is produced by a single coil stent. Thereby, the double coil open-form stent may allow for a more direct pathway for the movement of air and mucous along the airway. In practice, such a double helix open-form stent may be placed in an airway of a bronchial tree to improve airflow.

As shown in FIG. 5C, for instance, double helix open-form stent 582 is placed in airway 580. Of note, although open-form stent 582 is shown within only a single portion of airway 580, it should be understood that open-form stent may extend into other portions of airway 580 and/or may extend into other airways altogether.

3. EXAMPLE DILATORY BALLOON

Figure 6A:
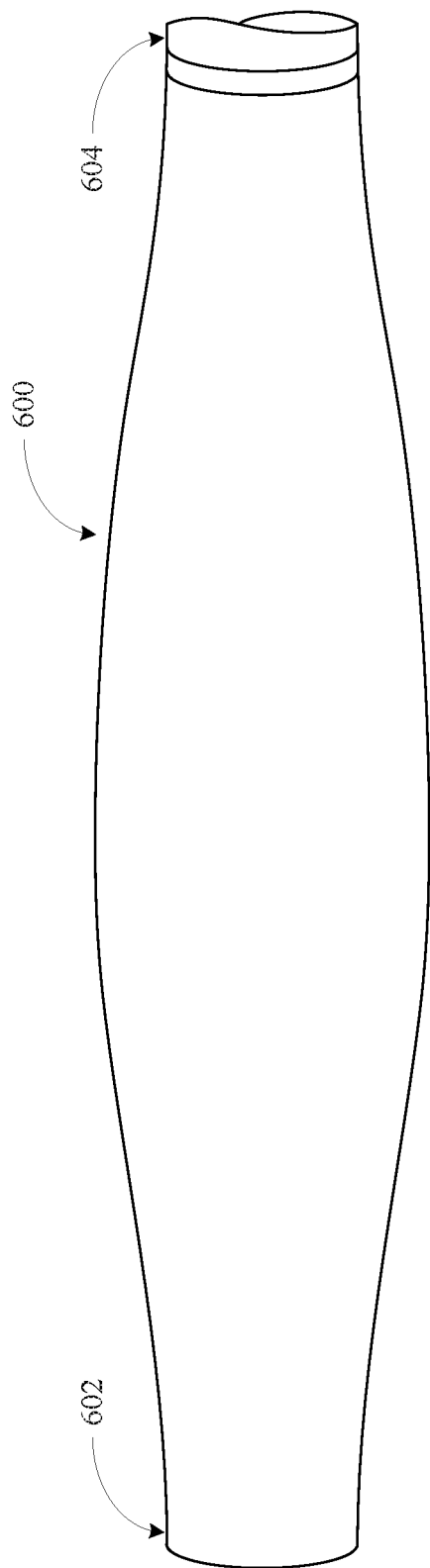
FIGS. 6A and 6B show aspects on an example expandable object.

FIG. 6A shows aspects of an example expandable object 600. As shown, the expandable object may generally be characterized by a resiliently flexible bulb, or other open body, that encloses an interior space.

Expandable object 600 may have a first end 602 that is closed and a second end 604 that is open. In another example, however, the first end may also be open. Either or both open ends may then be coupled to other extensions or connected objects, such as tubing, that permit communication of fluids such as gases and/or liquids into and out of the interior space of expandable object 600.

The expandable object may be formed of any suitable material. For instance, the expandable object may be formed of a one or more or silicone, polyvinyl chloride (PVC), nylon, polyethylene terephthalate (PET), polyether block amide (PEBAX), mylar, and/or latex. Other examples of suitable materials exist.

The expandable object may be coated in any suitable material. For instance, the expandable object may be coated in an antiproliferative agent (such as taxotere, paclitaxel, and/or sirolimus, among other examples). Notably, such an antiproliferative agent may generally assist in maintaining the patency of any tear or perforation formed in the airway wall by use of the expandable object. In this way, such an antiproliferative agent may help ensure the effectiveness of a treatment, particularly when the treatment does not involve the placement of a stent. Additionally and/or alternatively, the expandable object may be coated in one or more of an antimucous agent, a mucolytic agent, and a hydrophilic agent. Other examples of suitable coatings exist.

Figure 6B:
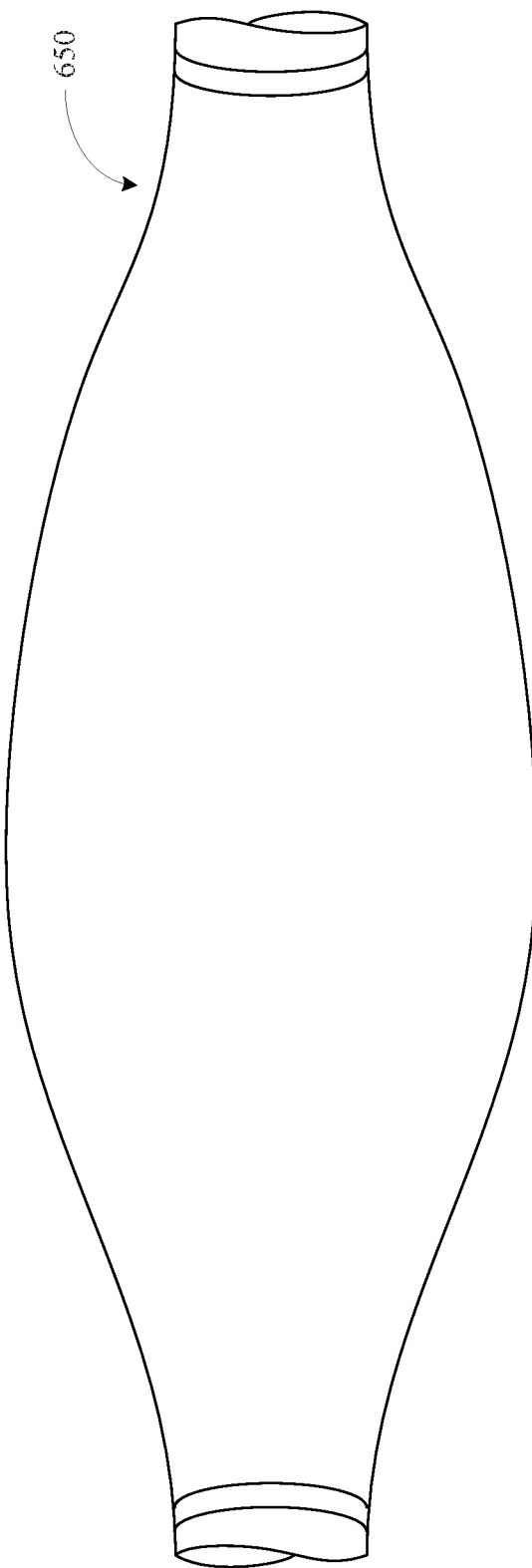

With reference to FIG. 6A, the expandable object 600 is shown in a relaxed state where the expandable object is not expanded. By comparison, with reference to FIG. 6B, example expandable object 650 is shown in an expanded state.

As discussed further bellow, in operation the expandable object may be placed in an airway or multiple connected airways that form a pathway from more central airways to more peripheral airways or alveoli and then expanded so as to also expand the airway or airways. As such, at times the expandable object may be referred to herein as a "dilatory balloon."

In some applications, the dilatory balloon may be used to intentionally dilate an airway(s) or portion of connected airways beyond its normal or natural diameter. In such a situation, the dilatory balloon may perforate, puncture, or otherwise damage the wall of an airway or portion of connected airways. In some cases, expansion of the dilatory balloon will operate to form generally longitudinal tears in the wall of an airway or portion of connected airways. Notably, such longitudinal tears will tend to run largely parallel to blood vessels, which themselves tend to run along the length of airways. As a result, trauma to blood vessels themselves will be minimized, and so will bleeding be minimized.

FIGS. 7A and 7B show an example expandable object within an airway. With respect to FIG. 7A, expandable object 700 is shown, in a relaxed state, introduced within airway 702. With respect to FIG. 7B, expandable object 700 is shown, in an expanded state, within airway 702. As shown expandable object 700 has extended airway 702 beyond its normal size and has introduced opening 704 into the wall of airway 702. This effect may occur in the wall of a single airway or to one or more walls of connected airways. Of note, although expandable object 700 is shown within only a single portion of airway 702, it should be understood that expandable object 700 may extend into other portions of airway 702 and/or may extend into other airways altogether.

While the example expandable object is shown in the figures as having a regular shape, other shapes may be possible. For example, the balloon may taper in size from one end to the other. As another example, the balloon may include a bulbous end that is relatively larger than another portion of the balloon body. As another example still, the balloon may include two bulbous ends. As yet another example, the balloon may include one or more irregular implements on its out surface such as a ridge or other obtrusion that may concentrate force generated during pressurization and expansion of the balloon and enable the balloon to more readily perforate an airway wall when expanded. Irregular shapes of the balloon may generally serve the purpose of extending the airway in desired ways so as to introduce desired openings into the airway.

In some applications the use of the dilatory balloon described herein may differ from prior uses of expandable objects within the bronchial tree, such as dilatory balloons used in bronchoplasty. For instance, whereas in a bronchoplasty application an expandable object is typically placed in a central airway, the dilatory balloon described herein may be used in more periphery airways such as those described above with respect to FIG. 2. As another example, whereas in bronchoplasty application an expandable object is typically used to expand an obstructed airway to its normal size, the dilatory balloon described herein may be used to expand the airway beyond its normal size and in some instances produce openings in an airway wall or in one or more connected airways. Openings introduced in the airway wall may therefore aid in improving airflow between alveoli and other more central airways.

Introduction of openings, such as perforations and/or tears, to the surface of the airway may lead to exposure of additional openings from the airway to alveoli. In this way, airflow within the airway to alveoli may be beneficially increased. Moreover, because peripheral airways are characterized by relatively few mucous membranes, occlusion of the perforation and/or tears will be minimized.

Introduction of the dilatory balloon into periphery airways for this purpose may be accomplished using a relatively quick and efficient medical procedure in which it may be placed directly into the airway, passed through a bronchoscope placed in the trachea or other airways, through a endotracheal tube placed in the trachea, a laryngeal mask airway placed in hypopharynx, among other access methods. In some instances, the procedure may be accomplished as an outpatient procedure. In this way, the procedure may be significantly more convenient and significantly less intrusive than other techniques for improving airflow.

Figure 7C:
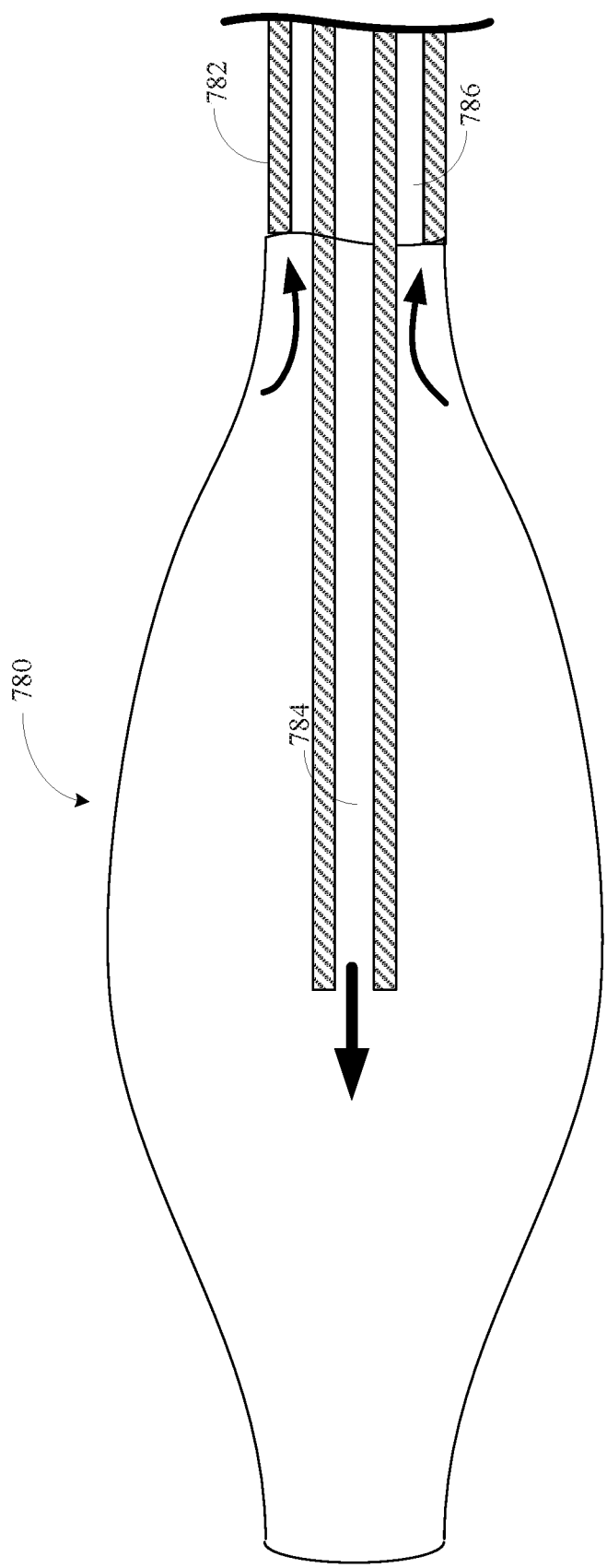
FIG. 7C shows aspects of an example expandable object.

In one example, the expandable object may take the form of a cryo balloon. FIG. 7C shows some aspects of an example cryo balloon 780 coupled, in fluid communication, with delivery catheter 782. As shown, catheter 782 may contain a fluid delivery passage 784 and fluid drain passage 786. Each of the walls of catheter 782, fluid delivery passage 784, and fluid drain passage 786 may be made from materials known to those skilled in the art. Aspects of example cryo balloon 780 have been simplified for purposes of example and explanation. Cryo balloon 780 may include other aspects as understood to those skilled in the art.

In use, cryo balloon 780 may be placed within a desired airway or a multiple connected airways of the bronchial tree. Coolant may then be released into the balloon from a pressurized cartridge, container, and/or pump (not shown) through fluid delivery passage 784 to cool the airway at a rate appropriate for the application. In some cases, coolant may be sprayed into the balloon through fluid delivery passage 784, a separate sprayer, or other suitable elements. The balloon may be inflated (e.g., by coolant) to a desired pressure (corresponding to a desired size). As a result, the temperature of the airway may be dropped. The resultant temperature will be below body temperature and, with potentially improved results below 0° C. and even more potentially improved results significantly below 0° C. By dropping the temperature of the balloon significantly below 0° C. the temperature of surrounding tissues may also be reduced significantly below 0° C. Reducing the temperature of surrounding tissues below 0° C. causes desiccation of the tissue and blood in surrounding blood vessels to stop flowing thereby destroying mucous cells in the airway walls, decreasing subsequent granulation tissue formation, and minimizing bleeding. The coolant may then later be discharged from the balloon through fluid drain passage 786.

The inflation fluid may be any suitable low freezing point liquid such as an ethanol mixture or saline mixture or a liquefied gas such as $N_2O$ or $CO_2$. Liquid $N_2$ can be used as a general purpose coolant. When $N_2$ is used, it can be transported to the balloon in the liquid phase where it evaporates at the exit of fluid delivery passage 784 and enters the balloon as a gas. Freon, $N_2O$ gas, and $CO_2$ gas can also be used as coolants. Other coolants could be used such as cold saline solution, Fluisol, or a mixture of saline solution and ethanol. Other examples of coolants exist.

While an example expandable object is discussed above as taking the form of a dilatory balloon, this is not necessary. The expandable object may take other forms as well. In one alternative example, the expandable object may take the form of a wire basket that is capable of decompressing and compressing. Such a wire basket may be well suited for causing perforations and/or tears in an airway wall in addition to expanding the airway wall.

4. FIRST EXAMPLE METHOD

Figure 8:
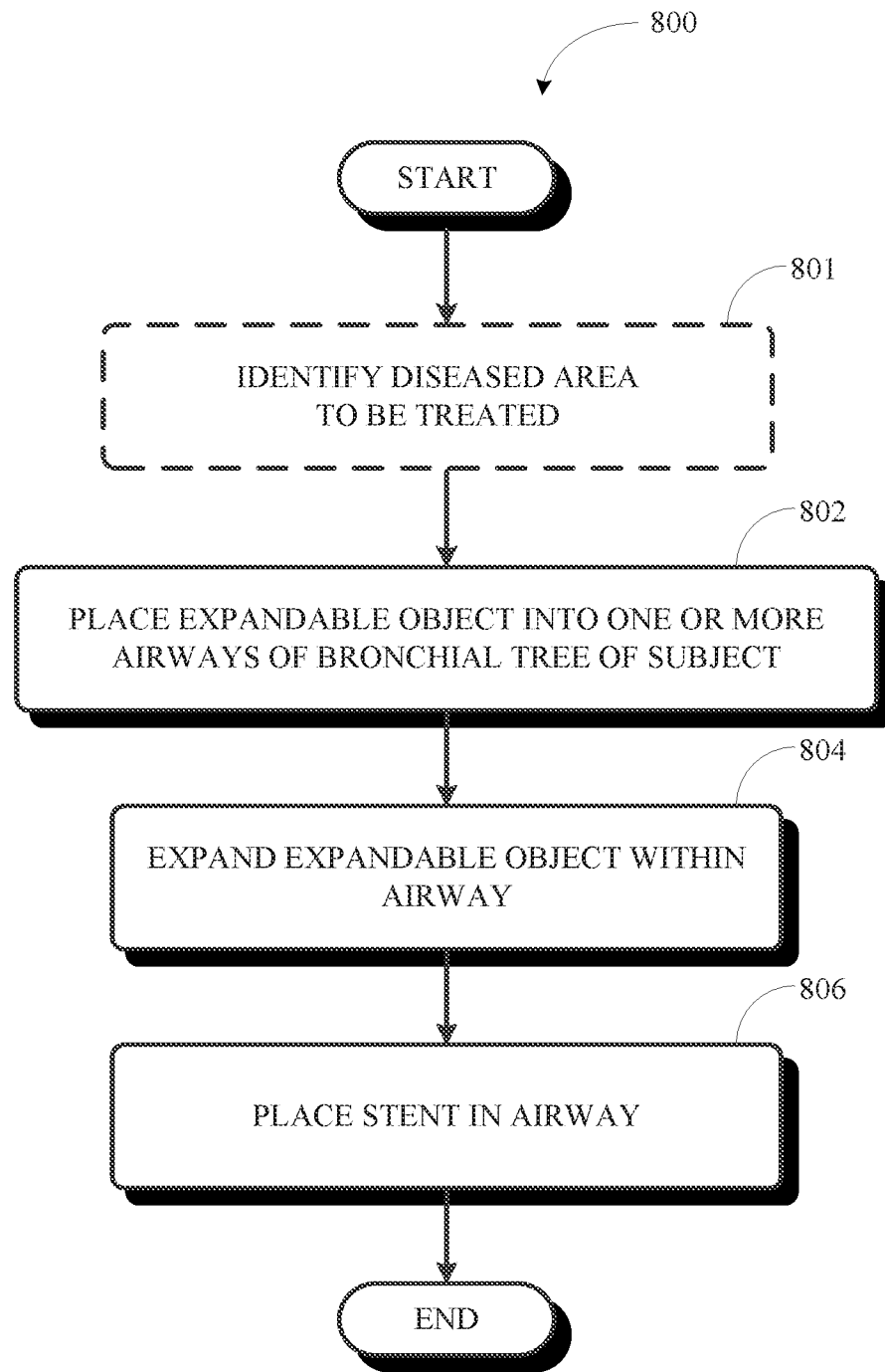
FIG. 8 shows an example method for improving airflow in an airway.

FIG. 8 generally shows an example method 800 for improving airflow within an airway.

For clarity, method 800 shown in FIG. 8 may be described herein with reference to the above figures. It should be understood, however, that this is for purposes of example and explanation only and that the operations of the methods should not be limited by these figures. Method 800 may include one or more operations, functions, or actions as illustrated by one or more of the blocks in each figure. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

Method 800 generally involves, at block 802 placing an expandable object into one or more airways of a bronchial tree of a subject. Block 804 includes expanding the expandable object within the airway. And block 806 includes placing a stent in the airway. As shown, method 800 may additionally/optionally involve, at block 801 identifying a diseased area to be treated.

Each of these blocks is discussed in more detail below.

a. Identify Diseased Area to be Treated

Block 801 involves identifying a diseased area to be treated. In accordance with block 801, a treating physician may identify the diseased area of a bronchial tree using any suitable technique including any such suitable technique known to those of skill in the art. In an example, the treating physician may identify a diseased area such as area 108 shown in FIG. 1.

b. Place Expandable Object into Airway of Bronchial Tree of Subject

Block 802 involves placing an expandable object into one or more airways of a bronchial tree of a subject. In accordance with block 802, the subject may be understood with respect to patient 100. In an example, the bronchial tree may be bronchial tree 106, and the one or more airways, or at least a portion thereof, may be an airway or portion of connected airways within diseased region 108 of the lung. In an example, block 802 involves placing the expandable object into the diseased area identified with respect to block 801.

In some examples, placing the expandable object may involve placing the expandable object into two or more airways of the bronchial tree of the subject. In such a situation, a first end of the expandable object is situated within a first airway of the bronchial tree and a second end of the expandable object is situated within a second airway of the bronchial tree.

The expandable object may be any suitable expandable object including, but not limited to, any one of the example expandable objects discussed above with respect to FIGS. 6A, 6B, 7A, 7B, and 7C.

In one example, the expandable object may include a dilatory balloon. Such a dilatory balloon may, in some instances, be a cryo balloon. In an example, the dilatory balloon may include a bulbous form on a distal end. In another example, the dilatory balloon may include at least a portion of its outer surface that is non-uniform. For instance, the outer surface may include a ridge and/or other obtrusion to aid in the expansion and/or formation of openings in an airway wall.

In an example, placing the expandable object may involve placing the expandable object using a delivery device such as a catheter, guide wire, bronchoscope and the like. In some instances, placing the expandable object may additionally involve identifying the targeted area of a diseased lung, and directing the expandable area towards the identified area such that at least a portion of the expandable object is near the diseased portion of the lung. As one having skill in the art will appreciate, the expandable object may be affixed to a distal end of the delivery catheter. A treating physician may then introduce the expandable object into the trachea 104 of the patient. Using the delivery catheter, the treating physician may then guide the expandable object through the bronchial tree and into a peripheral airway of the bronchial tree. The distal end of the expandable object may ultimately be delivered to a peripheral diseased region 108, and into a respiratory bronchiole 206 while the proximal end of the expandable object remains in a more proximal airway such as a terminal bronchiole, conducting bronchiole, bronchiole, sub-segmental bronchus, segmental bronchus or lobar bronchus.

Figure 9A:
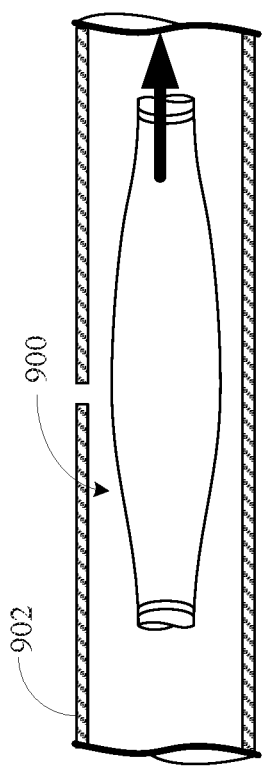
FIGS. 9A, 9B, 9C, 9D, 9E, 9F, and 9G show example aspects of example methods.
Figure 9B:
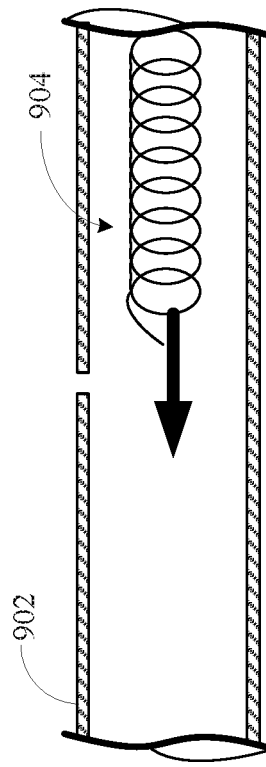

Aspects of block 802 are shown with respect to FIGS. 9A and 9B. With respect to FIG. 9A, expandable object 900 is shown as being guided into airway 902. With respect to FIG. 9B, expandable object 900 is shown as having been placed in a desired location of airway 902.

As discussed above and further below with respect to FIG. 9G, an alternative example placement of an expandable object may involve placing the expandable object within the bronchial tree such that the expandable object spans multiple types of airways. For instance, as shown in FIG. 9G, expandable object 912 is placed within bronchial tree 910 such that the distal end of expandable object 912 is situated within a respiratory bronchiole and such that the proximal end is extending proximally into larger and more central airways.

c. Expand Expandable Object within Airway

Block 804 involves expanding the expandable object within the airway such that at least a portion of the airway or a portion of connected airways is expanded. In some cases, at least one opening is formed in a wall of the airway as a result of the expansion of the expandable object.

In some examples, expanding the expandable object may involve expanding the expandable object within at least two of two or more airways such that at least a portion of a wall of the two or more airways is expanded.

As discussed above, the expandable object may be expanded by introducing fluid such as liquid and/or gas, into the expandable object. For instance, in an example where the expandable object is a cryo balloon, the cryo balloon may be expanded by introducing $N_2O$ into the cryo balloon.

Figure 9C:
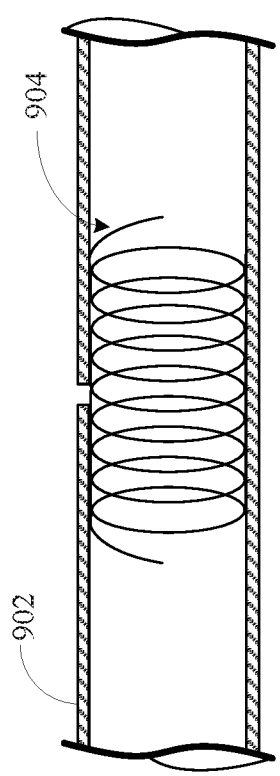

Aspects of block 804 are shown with respect to FIG. 9C. As shown in FIG. 9C, expandable object 900 has been expanded such that airway 902 is expanded beyond its normal size. As a result, in the particular example shown, the expandable object has caused airway 902 to tear such that an opening is now present in the airway wall.

While a tear is shown as formed in airway 902, it should be understood that it is not necessary to form an opening in all implementations. In some implementations it may be desirable and/or sufficient to dilate the airway without tearing the airway.

Further, while a single tear is shown as formed in airway 902, it should be understood that more than one tear may be formed. That is, block 804 may involve forming at least one opening in the airway wall.

Further, with reference again to FIG. 9G, expandable object 912 may be expanded such that multiple sections of airways of bronchial tree 910 are expanded. In turn, tears and/or perforations may be formed within multiple sections of airways.

Figure 9D:
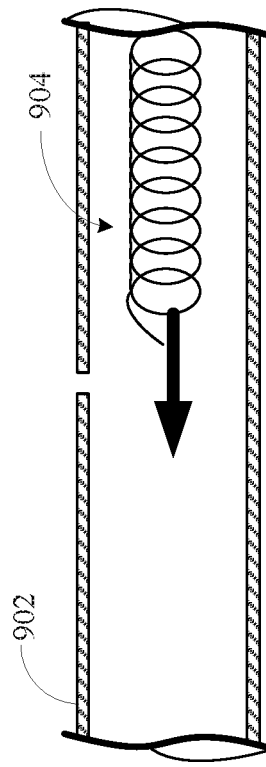

In some implementations, after the expandable object is expanded, the expandable object may then be removed. As shown with respect to FIG. 9D, expandable object 900 has been returned to a relaxed state. Expandable object 900 may then be guided out of the airway, back through the bronchial tree, and out of the patient's trachea.

d. Place Stent in Airway

Block 806 involves placing a stent in the airway such that a portion of the stent is adjacent to the portion of the wall of the one or more expanded airways. In an implementation where the airway wall was torn in accordance with block 804, placing the stent may involve placing the stent in the airway such that a portion of the stent is adjacent to at least a portion of the opening in the wall of the airway.

In some examples, placing a stent may involve placing the stent within at least two of two or more airways such that a portion of the stent is adjacent to a portion of two or more expanded airways.

The stent may be any suitable stent including, but not limited to, any one of the open-form stents discussed above with respect to FIGS. 3A, 3B, 4A, 4B, 5A, 5B, and 5C.

For instance, at least a portion of the open form stent may include a coil. And in some cases, the stent may include both a first coil and a second coil.

In one example, the open form stent has an open form wall, as discussed above. In such an example, for at least a particular length of the open-form stent, no portion of the open-form wall entirely isolates a given area of the open-form wall. As such, the open-form wall may have a continuously open helical surface along its length.

While examples described herein include the placement of an open-form stent, it should be understood that in some cases the method may be carried out using a more traditional closed-form stent. In such cases, block 806 may involve placing a closed form stent.

Figure 9E:
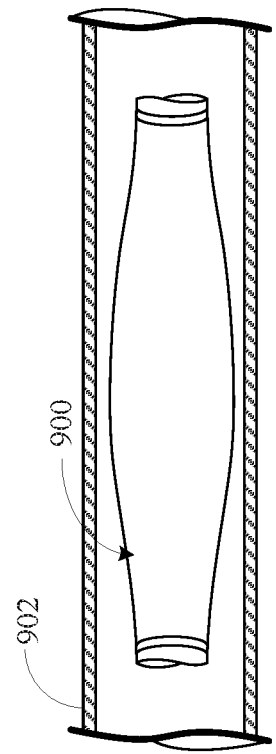
Figure 9F:
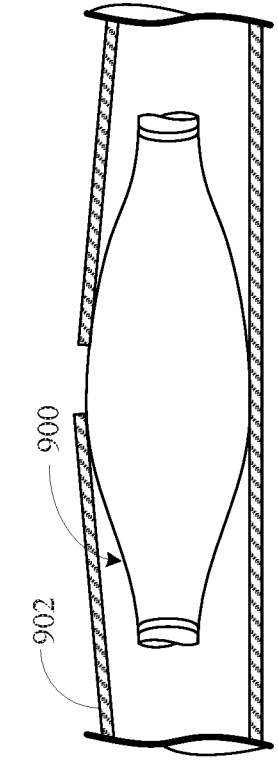
Figure 9G:
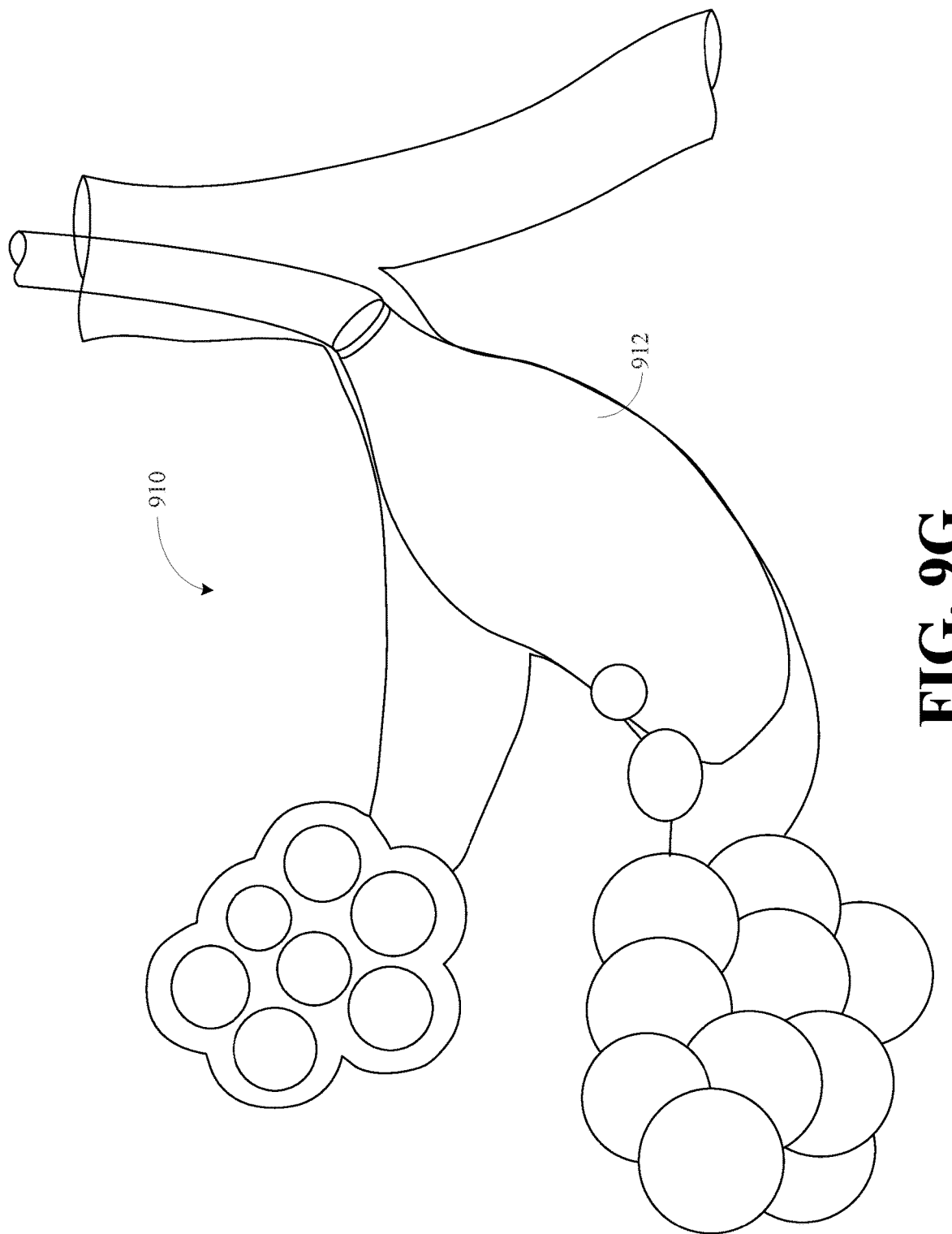

Aspects of block 806 are shown with respect to FIGS. 9E and 9F. With respect to FIG. 9E, open-form stent 904 is shown as being guided into airway 902. As shown, while being guided into place, open-form stent may be held in a compressed form to aid in maneuverability through the bronchial tree. With respect to FIG. 9E, open-form stent 904 is shown as having been placed in a desired location of airway 902 and permitted to expand. As shown, open-form stent 904 has been placed adjacent to the opening in airway 902.

Open-form stent 904 may then be left in the airway indefinitely and/or until a treating physician determines to remove the open-form stent. Alternatively, the open-form stent may be placed temporarily and removed after some predetermined amount of time. In this way, removal of the open-form stent will leave an open tissue conduit between central airways and the alveoli.

In the example shown above, an embodiment of method 800 is described where the expandable object is removed from the airway before the stent is placed in the airway. However, this is not necessary. In another embodiment of method 800, the expandable object may be placed together with the stent. Example aspects of such an embodiment are shown with respect to FIGS. 10A, 10B, 10C, 10D, 10E, and 10F.

Figure 10A:
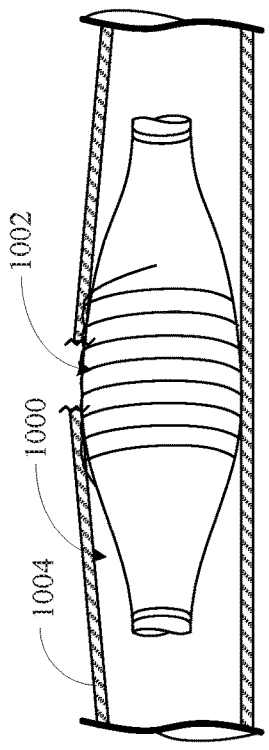
FIGS. 10A, 10B, 10C, 10D, 10E, and 10F show example aspects of example methods.

As shown with respect to FIG. 10A, before placing the expandable object 1000, the stent 1002 may be positioned so as to encompass at least a portion of the expandable object. In this way, the expandable object 1000 and stent 1002 form a package that may together be guided into an airway.

Figure 10D:
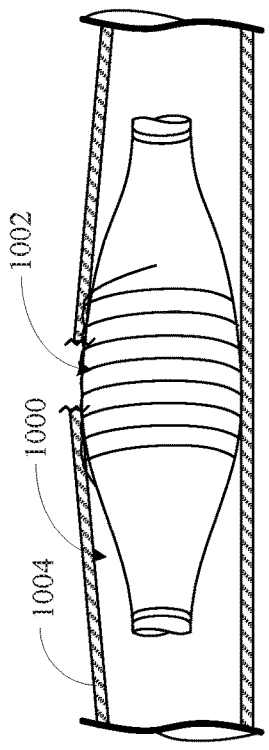
Figure 10B:
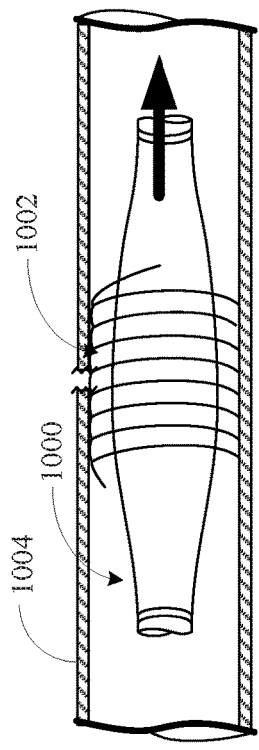

With respect to FIG. 10B, the package of expandable object 1000 and stent 1002 may then be guided into airway 1004. As shown in FIG. 10C, the package of expandable object 1000 and stent 1002 has been placed in a desired location of the airway.

With respect to FIG. 10D, the expandable object 1000 may then be expanded. As shown, stent 1002 may be arranged so that it increases in size as expandable object 1000 expands. After expansion of expandable object 1000, an opening in airway 1004 is formed.

Figure 10E:
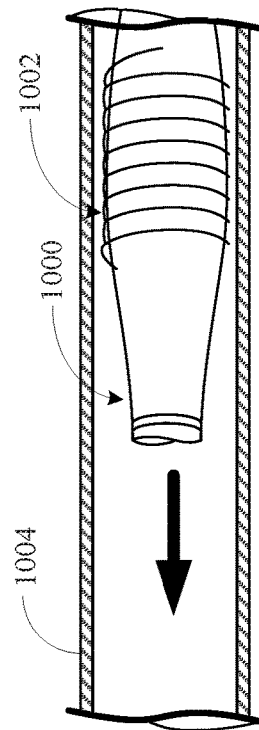
Figure 10C:
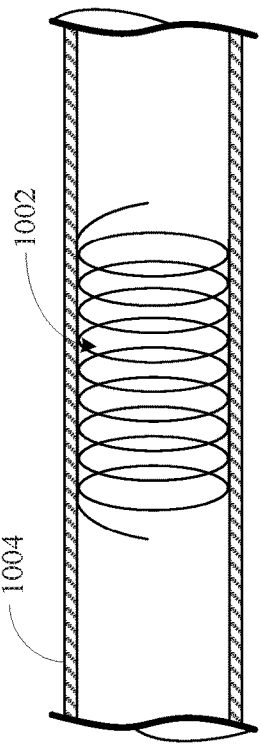

With respect to FIG. 10E, the expandable object 1000 may then be returned to a relaxed state. At the same time, open-form stent 1002 may maintain a decompressed form, such that it now exerts radial tension on the airway or portion of connected airways. As shown in FIG. 10E, open-form stent 1004 may exert such radial tension on the airway or portion of connected airways adjacent to at least a portion of the at least one opening that was formed. Once expandable object 1000 is returned to a relaxed state, it may then be guided out of the airway, back through the bronchial tree, and out of the patient's trachea.

Figure 10F:
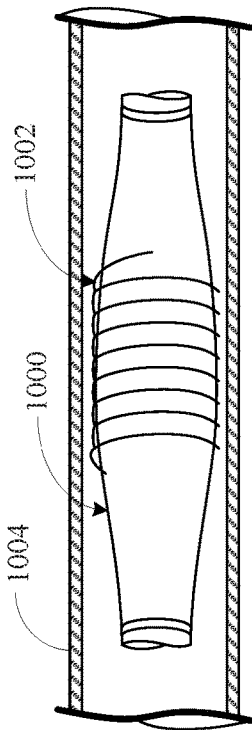

With respect to FIG. 10F, once expandable object 1000 is removed from the airway, stent 1002 may remain in place within airway 1004 or portion of connected airways. Further, in some examples stent 1002 may remain in place within the bronchial tree such that the stent spans multiple types of airways. For instance, in some ways similar to expandable object 912 shown in FIG. 9G, stent 1002 may be placed within a bronchial tree such that the distal end of the stent is situated within a respiratory bronchiole and such that the proximal end is extending proximally into larger and more central airways.

5. SECOND EXAMPLE METHOD

It should be understood that, while various functions described above are described, at times, as performed together as part of the same method, this is not necessary. In some cases, for instance, a stent such as that described herein may be used without the use of an expandable object. On the other hand, an expandable object such as that described herein may be used without the use of a stent. Other examples may exist.

Figure 11:
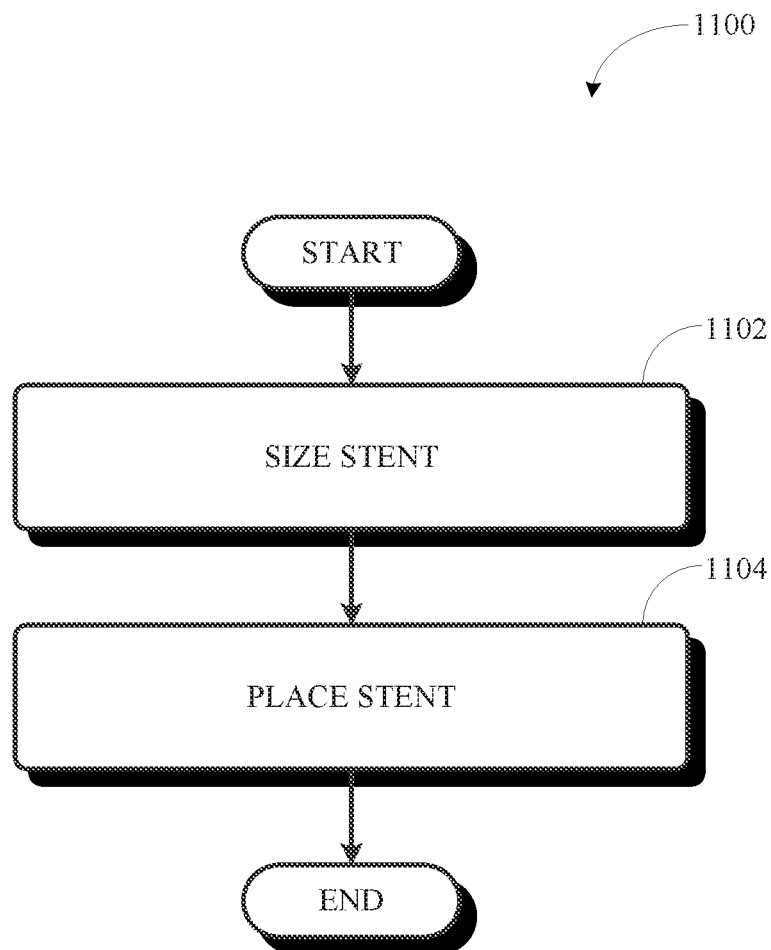
FIG. 11 shows an example method for improving airflow in an airway.

FIG. 11 generally shows another example method 1100 for improving airflow within an airway or portion of a series of connected airways.

For clarity, method 1100 shown in FIG. 11 may be described herein with reference to various other figures. It should be understood, however, that this is for purposes of example and explanation only and that the operations of the methods should not be limited by these figures. Method 1100 may include one or more operations, functions, or actions as illustrated by one or more of the blocks in each figure. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

Method 1100 generally involves, at block 1102, sizing an open-form stent. Block 1104 includes placing the open form stent.

a. Size Stent

Block 1102 involves sizing a stent. The size of the stent may be characterized by estimates of both diameter of the stent and length of the stent.

The open-form stent may be any suitable stent including, but not limited to, any one of the open-form stents discussed above with respect to FIGS. 3A, 3B, 4A, 4B, 5A, 5B, and 5C.

In accordance with block 1102, the stent may be sized according to any suitable technique.

In one example, the stent may be sized based on an approximated size of an airway that the stent is to be placed into. For instance, a size corresponding to an average size of a respiratory bronchiole may be used. As another example, a size corresponding to the diameter of the most proximal airway in which the stent is to be placed may be used.

In another example, the open-form stent may be sized based on an image of a given patient's bronchial tree. For instance, the patient's bronchial tree may be imaged prior to placement of the stent using known imaging techniques and the stent may be sized according to a size indicated by the image. Or, for example, distances can be estimated from images generated using known imaging techniques of the patient's chest during the actual procedure.

In yet another example, the stent may be sized using an expandable object such as an expandable object described elsewhere herein. For instance, prior to placement of the stent, the expandable object may be placed within the airway and expanded. Then, a size of the expandable object in the expanded state may be used to infer an appropriate size for the stent. In one example, a pressure of the expandable object may be measured when the expandable object is in the expanded state. The pressure may be measured using a pressure gauge located on the proximal end of a delivery system for the expandable object. The measured pressure may be correlated to an appropriate size for the stent.

b. Place Open-Form Stent

Block 1104 involves placing the stent in one or more airways. In accordance with block 1104, the stent may be placed in any suitable manner. For instance, the stent may be placed in accordance with the description above associated with FIGS. 9E and 9F.

6. THIRD EXAMPLE METHOD

Figure 12:
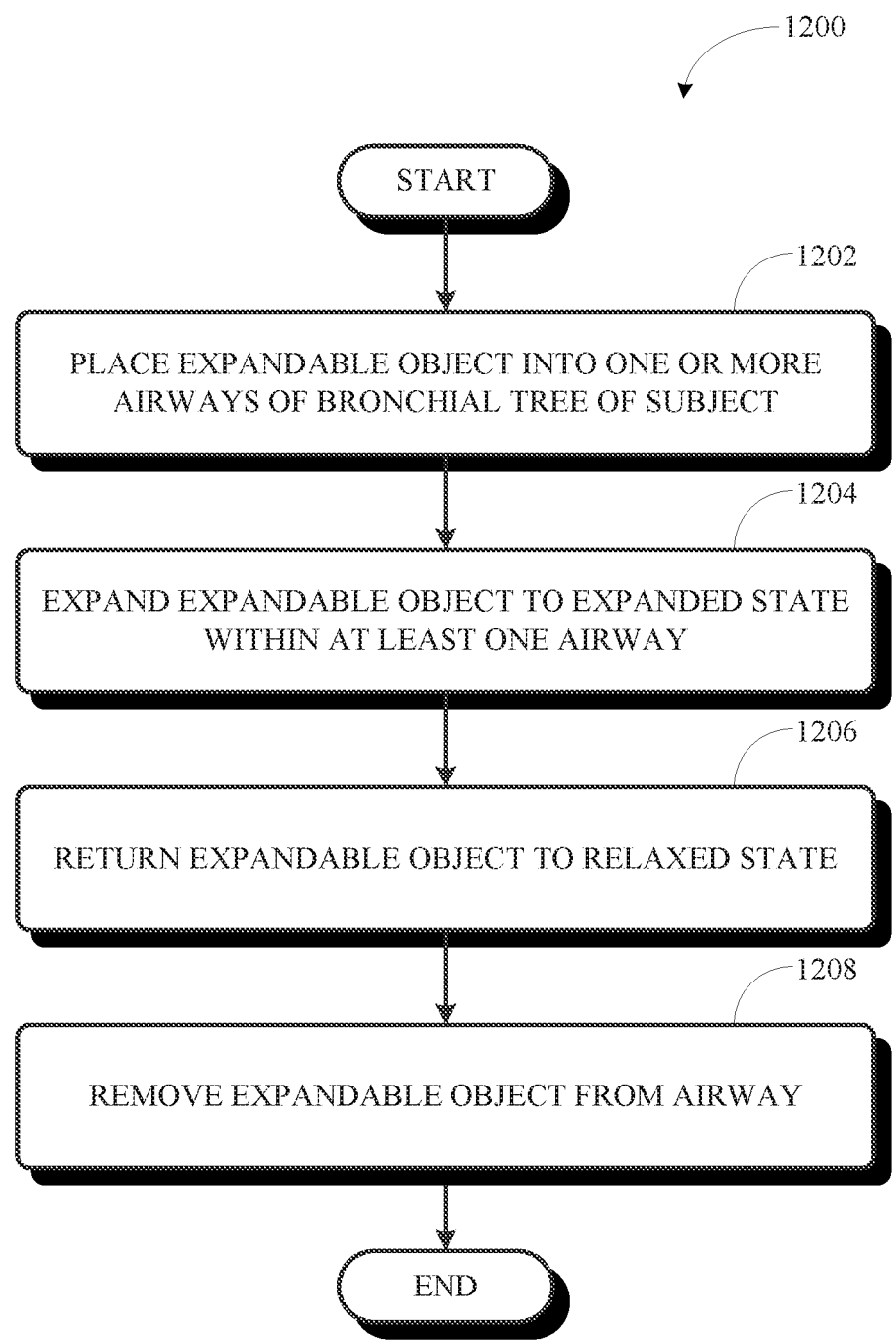
FIG. 12 shows an example method for improving airflow in an airway.

FIG. 12 generally shows another example method 1200 for improving airflow within an airway.

For clarity, method 1200 shown in FIG. 12 may be described herein with reference to various other figures. It should be understood, however, that this is for purposes of example and explanation only and that the operations of the methods should not be limited by these figures. Method 1200 may include one or more operations, functions, or actions as illustrated by one or more of the blocks in each figure. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

Method 1200 generally involves, at block 1202, placing an expandable object into one or more airways of a bronchial tree of a subject. Block 1204 includes expanding the expandable object from a relaxed state to an expanded state within at least one of the one or more airways. Block 1206 includes returning the expandable object from the expanded state to the relaxed state. And block 1208 includes removing the expandable object form the bronchiole.

a. Place Expandable Object into Airway of Bronchial Tree of Subject

Block 1202 involves placing an expandable object into one or more airways of a bronchial tree of a subject. The expandable object may be placed using any suitable technique including those described herein. For instance, the expandable object may be placed as shown above with respect to FIGS. 9A and 9B or FIGS. 10B and 10C.

b. Expand Expandable Object to Expanded State within Airway

Block 1204 involves expanding the expandable object from a relaxed state to an expanded state within at least one of the one or more airways such that at least a portion of the airway or connected airways is expanded. In some cases, at least one opening is formed in a wall of the one or more airways as a result of the expansion of the expandable object. The expandable object may be expanded within the airway using any suitable technique including those described herein. For instance, the expandable object may be expanded as shown above with respect to FIG. 9C and FIG. 10D.

In some instances, the expandable object may be sized such that the expandable object, when expanded, assumes an outer diameter similar to that described above with reference to the stents.

c. Return Expandable Object to Relaxed State

Block 1206 involves returning the expandable object from the expanded state to the relaxed state. The expandable object may be returned to the relaxed state using any suitable technique including those described herein. For instance, the expandable object may be returned to the relaxed state as shown above with respect to FIG. 9D and FIG. 10E.

d. Remove Expandable Object from Airway

Block 1208 involves removing the expandable object from the one or more airways The expandable object may be removed using any suitable technique including those described herein. For instance, the expandable object may be removed as shown with respect to FIG. 9D and FIG. 10E.

7. EXAMPLE TREATMENT PROTOCOL

Figure 13:
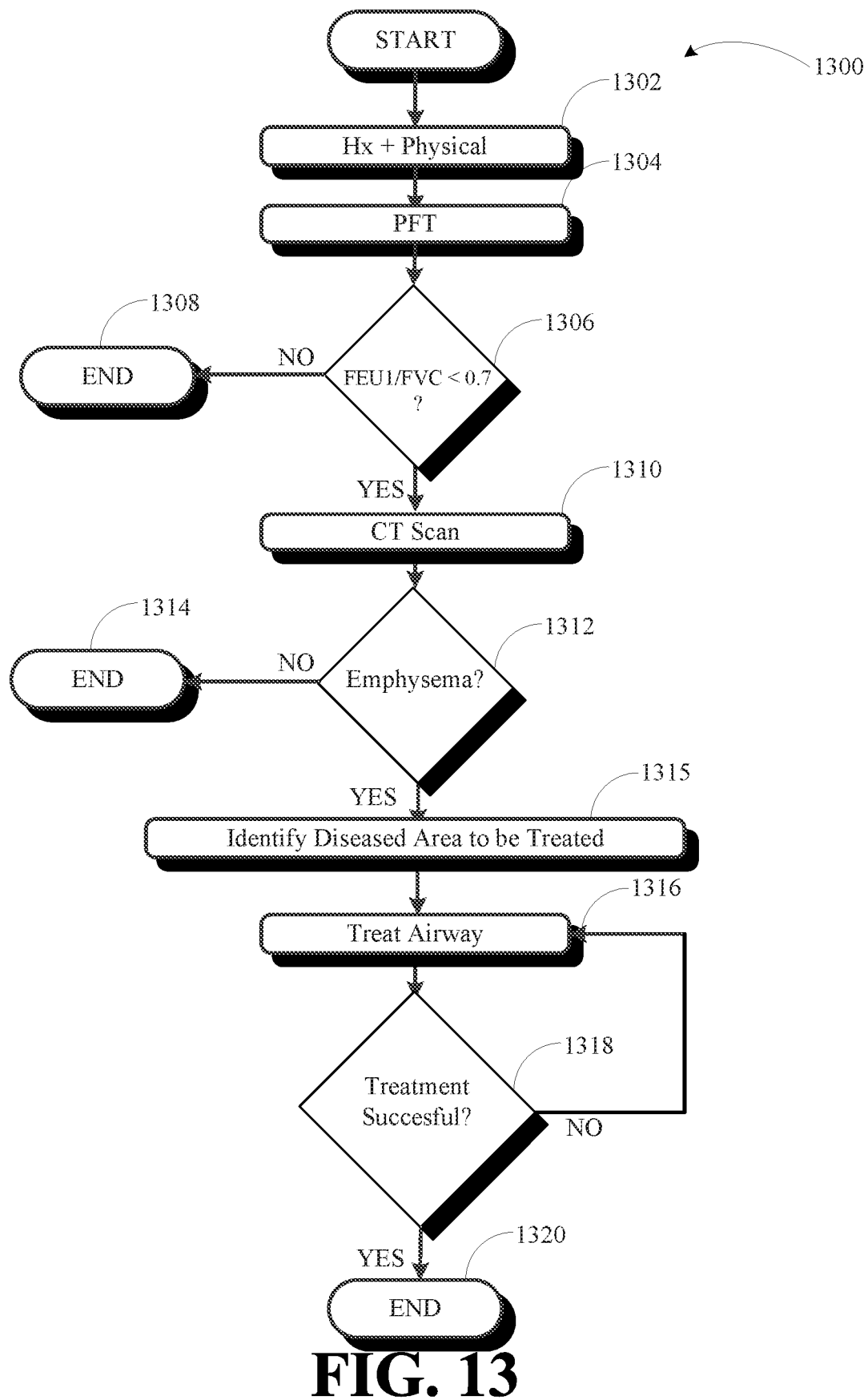
FIG. 13 shows an example treatment protocol.

FIG. 13 generally shows an example treatment protocol 1300 that may be used in conjunction with the various techniques described herein for improving airflow within an airway. While certain functions are described with respect to treatment protocol 1300, it should be understood that additional and/or other functions may be performed as well.

Treatment protocol 1300 begins at block 1302, where a patient is given a pulmonary history and physical. If the pulmonary history (Hx) and/or physical indicate that there is a possibility of lung disease, the protocol continues to block 1304.

At block 1304, the patient is given a pulmonary function test (PFT). The PFT may include a battery of tests including but not limited to spirometry, static lung volume measurement, diffusing capacity for carbon monoxide, airways resistance, respiratory muscle strength, and arterial blood gases, among other examples.

At block 1306, it is determined whether the patient's ratio of force expiratory volume (FEV) in one second to force to vital capacity (FVC) is greater than 0.7. If no, the protocol proceeds to block 1308, where it ends. If yes, the protocol proceeds to block 1310. Notably, other criteria could be used for the decision point at block 1306. For instance, if there exists evidence of severe hyperinflation (where the ratio of residual volume (RV) to total lung capacity (TLC) is greater than or equal to 0.65), then the protocol may proceed to block 1310.

At block 1310, the patient is given a CT scan. The CT scan image and data is then analyzed by the treating physician.

At block 1312, it is determined whether the patient's CT scan chart indicates that the patient has lung disease such as emphysema, whether homogeneous or heterogeneous. If no, the protocol proceeds to block 1314, where it ends. If yes, the protocol proceeds to block 1316. In some situations, it may further be determined that there exists no evidence of significant airway disease or no isolated airway disease without concurrent emphysema before proceeding to block 1316.

At block 1315, the treating physician identifies a diseased area to be treated. In accordance with block 1315, a treating physician may identify the diseased area of a bronchial tree using any suitable technique including any such suitable technique known to those of skill in the art. In an example, the treating physician may identify a diseased area such as area 108 shown in FIG. 1.

At block 1316, the treating physician treats one or more airways within the patient's bronchial tree so as to improve airflow. The airway may be treated in accordance to any method for improving airflow within an airway described herein including, for example, one or more of method 800, method 1100, and method 1200.

At block 1318, it is determined whether the treatment was successful in improving airflow. If yes, the protocol proceeds to block 1320 where it ends. If no, block 1316 is repeated so as to improve airflow.

8. EXAMPLE TREATMENT PROTOCOL

In an embodiment, a system may be provided in accordance with the various methods described herein. The system may include one or more of an expandable object, a stent, and instructions for improving airflow in an airway of a bronchial tree.

The stent may be any of the stents described herein such as those described with respect to FIGS. 3A, 3B, 4A, 4B, 5A, 5B, and 5C. The expandable object may be any of the expandable objects described herein such as those described with respect to FIGS. 6A, 6B, 7A, 7B, and 7C. The instructions for improving airflow may correspond to any of the example methods for improving airflow described herein such as any of methods 800, 1100, and 1200.

The system may further include other objects. One example includes a cartridge containing compressed and/or liquefied gas used for expanding the expandable object. Another example includes a pressure gauge used for monitoring the pressure within the expandable object. Yet another example includes one or more delivery catheter used for guiding the expandable object and/or the stent through the bronchial tree.

9. CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A method comprising:
   identifying a diseased portion of an emphysematous lung that is located at a terminal portion of a bronchial tree within the emphysematous lung;
   placing a stent into a pathway of two or more connected airways in the emphysematous lung having (a) a first airway at a distal end of the pathway within the terminal portion of the bronchial tree at which the diseased portion is located and (b) a second airway at a proximal end of the pathway that is of a lower generation than the first airway, wherein a distal end of the stent is positioned within the first airway and a proximal end of the stent is positioned in the second airway; and
   with the stent, holding at least a portion of the pathway of two or more connected airways at a diameter that is greater than a normal, pre-diseased diameter of the portion of the pathway of two or more connected airways.

2. The method of claim 1, wherein the stent is an open-form stent.

3. The method of claim 1, wherein the stent is placed within the two or more connected airways such that no portion of the stent is placed outside of the respective airway walls of the two or more connected airways.

4. The method of claim 1, wherein the open-form stent comprises a continuously open helical surface.

5. The method of claim 1, wherein the stent does not totally block a mucociliary structure of the pathway of two or more connected airways in any one direction.

6. The method of claim 1, wherein the stent comprises a single helical strand.

7. The method of claim 1, wherein the diseased portion of the emphysematous lung is hyperinflated.

8. The method of claim 1, wherein the diseased portion of the emphysematous lung comprises at least one of alveoli, alveolar ducts, or respiratory bronchi with irreversibly destructed alveolar walls.

9. The method of claim 1, wherein the second airway is one of a conducting bronchiole, bronchiole, sub-segmental bronchus, segmental bronchus, lobar bronchus, or main bronchus.

10. The method of claim 1, wherein the diseased portion of the emphysematous lung comprises trapped air.

11. The method of claim 10, wherein placing the stent into the pathway of two or more connected airways reduces air trapping in the diseased portion of the emphysematous lung.

12. A method comprising:
    placing a stent into a pathway of connected airways in an emphysematous lung, at least a portion of the pathway comprising diseased airway tissue, the pathway having (a) a first airway at a distal end of the pathway that comprises a bronchiole at which at least some of the diseased airway tissue is located, (b) a second airway at a proximal end of the pathway that comprises a bronchus, and (c) a plurality of intermediate airways located between the first and second airways, wherein the stent has a proximal end, a distal end, and an intermediate region between the proximal and distal ends, and wherein the stent is placed such that the distal end of the stent is positioned within the first airway, the proximal end of the stent is positioned within the second airway, and the intermediate region is positioned along the plurality of intermediate airways;
    with the stent, holding at least a portion of the pathway of connected airways at a diameter that is greater than a normal, pre-diseased diameter of the portion of the pathway of connected airways.

13. The method of claim 12, wherein the stent is an open-form stent.

14. The method of claim 12, wherein the stent is placed within the connected airways such that no portion of the stent is placed outside of the respective airway walls of the connected airways.

15. The method of claim 12, wherein the open-form stent comprises a continuously open helical surface.

16. The method of claim 12, wherein the stent does not totally block a mucociliary structure of the pathway of connected airways in any one direction.

17. The method of claim 12, wherein the stent comprises a single helical strand.

18. The method of claim 12, wherein the diseased airway tissue is hyperinflated.

19. The method of claim 12, wherein the diseased airway tissue comprises at least one of alveoli, alveolar ducts, or respiratory bronchi with irreversibly destructed alveolar walls.

20. The method of claim 12, wherein the second airway is one of a sub-segmental bronchus, segmental bronchus, lobar bronchus, or main bronchus.

21. The method of claim 12, wherein the diseased airway tissue comprises trapped air.

* * * * *